United States Patent [19]
Murtaugh et al.

[11] Patent Number: 5,998,601
[45] Date of Patent: Dec. 7, 1999

[54] VR-2332 VIRAL NUCLEOTIDE SEQUENCE AND METHODS OF USE

[75] Inventors: Michael P. Murtaugh, Roseville; Margaret R. Elam, Minneapolis; Laura T. Kakach, Hopkins, all of Minn.

[73] Assignee: Regents of The University of Minnesota, Minneapolis, Minn.

[21] Appl. No.: 08/799,464

[22] Filed: Feb. 13, 1997

Related U.S. Application Data

[63] Continuation of application No. 08/287,941, Aug. 5, 1994, abandoned.

[51] Int. Cl.$^6$ .......................... C07H 21/04; A61K 39/02; A61K 39/12
[52] U.S. Cl. .................. 536/23.72; 536/23.1; 424/199.1; 424/204.1
[58] Field of Search ................................. 424/186.1, 815, 424/218.1, 199.1, 204.1; 435/320.1; 536/23.72, 24.3, 24.33, 23.1

[56] References Cited

FOREIGN PATENT DOCUMENTS

| 0595436 A2 | 4/1994 | European Pat. Off. ....... A61K 39/12 |
| 9303760 | 3/1993 | WIPO ............................. A61K 39/12 |

OTHER PUBLICATIONS

Benfield et al. Characterization of swine infertility and respiratory syndrome(SIRS) virus (isolate ATCC VR–2332). J.Vet.Diagn.Invest. vol. 4:127–133, 1992.

Conzelmann et al. "Molecular Characterization of Porcine Reproductive and Respiratory Syndrome Virus, a Member of the Arterivirus Group". Virology. 193:329–339, 1993.

Meulenberg et al. "Lelystad Virus, the Causative Agent of Porcine Epidemic Abortion and Respiratory Syndrome–(PEARS), Is Related to LDV and EAV". Virology. 192:62–72, 1993.

Attachment A–sequence search.

Shibata et al J. Exp. Med. 167:225–230, 1988.

Suarez et al Arch. Vir. 135:89–99, 1994.

Benfield et al J. Vet. Diagn. Invest. 4:127–133, 1992.

Klupp et al Virology 182:732–741, 1991.

Ellis, Chapter 29 in Vaccines, Polotkin et al Eds., WB Saunders.

*Primary Examiner*—Lynette F. Smith
*Assistant Examiner*—Datquan Lee
*Attorney, Agent, or Firm*—Hovey, Williams, Timmons & Collins

[57] ABSTRACT

A nucleotide sequence is provided for the VR-2332 virus, which is capable of causing Porcine Reproductive and Respiratory Syndrome. The nucleotide sequence includes protein coding regions that are inserted into recombinant vectors for the host expression of viral proteins according to a variety of vaccination techniques. Diagnostic assays utilize fragmentary sequences or oligonucleotides to selectively identify the VR-2332 nucleic acids by hybridization or PCR amplification reactions that distinguish VR-2332 nucleotide sequences from other PRRS-causative viruses which are immunologically distinct from VR-2332.

3 Claims, 11 Drawing Sheets

```
        V  E  F  S  L  P  T  H  H  T  V  R  L  I  R  V  T  A  S  P
3121  TGGAGTTTAGTTTGCCTACGCATCATACTGTGCGCCTGATCCGCGTCACAGCATCACCCT
        S  A  *
3181  CAGCATGATGGGCTGGCATTCTTGAGGCATCTCAGTGTTTGAATTGGAAGAATGTGTGGT
3241  GAATGGCACTGATTGACATTGTGCCTCTAAGTCACCTATTCAATTAGGGCGACCGTGTGG
3301  GGGTGAGATTTAATTGGCGAGAACCATGCGGCCGAAATTAAAAAAAAAAAAAAAAAAA
```

Fig. 2A.

```
ORF 2      M  K  W  G  P  C  K  A  F  L  T  K  L  A  N  F  L  W  M  L
      1  ATGAAATGGGGTCCATGCAAAGCCTTTTTGACAAAATTGGCCAACTTTTTGTGGATGCTT
           S  R  S  S  W  C  P  L  L  I  S  L  Y  F  W  P  F  C  L  A
     61  TCACGGAGTTCTTGGTGTCCATTGTTGATATCATTATATTTTTGGCCATTTTGTTTGGCT
           S  P  S  P  V  G  W  W  S  F  A  S  D  W  F  A  P  R  Y  S
    121  TCACCATCGCCGGTTGGCTGGTGGTCTTTTGCATCAGATTGGTTTGCTCCGCGATACTCC
           V  R  A  L  P  F  T  L  S  N  Y  R  R  S  Y  E  A  F  L  S
    181  GTACGCGCCCTGCCATTCACTCTGAGCAATTACAGAAGATCTTATGAGGCCTTTCTTTCC
           Q  C  Q  V  D  I  P  T  W  G  T  K  H  P  L  G  M  L  W  H
    241  CAGTGCCAAGTGGACATTCCCACCTGGGGAACTAAACATCCCTTTGGGATGCTTTGGCAC
           H  K  V  S  T  L  I  D  E  M  V  S  R  R  M  Y  R  I  M  E
    301  CATAAGGTGTCAACCCTGATTGATGAAATGGTGTCGCGTCGAATGTACCGCATCATGGAA
           K  A  G  Q  A  A  W  K  Q  V  V  S  E  A  T  L  S  R  I  S
    361  AAAGCAGGGCAGGCTGCCTGGAAACAGGTGGTGAGCGAGGCTACGCTGTCTCGCATTAGT
           S  L  D  V  V  A  H  F  Q  H  L  A  A  I  E  A  E  T  C  K
    421  AGTTTGGATGTGGTGGCTCATTTTCAGCATCTAGCCGCCATTGAAGCCGAGACCTGTAAA
           Y  L  A  S  R  L  P  M  L  H  N  L  R  M  T  G  S  N  V  T
    481  TATTTGGCCTCCCGGCTGCCCATGCTACACAACCTGCGCATGACAGGGTCAAATGTAACC
           I  V  Y  N  S  T  L  N  Q  V  F  A  I  F  P  T  P  G  S  R
    541  ATAGTGTATAATAGCACTTTGAATCAGGTGTTTGCTATTTTTCCAACCCCTGGTTCCCGG
ORF 3                                      M  V  N  S  C  T  F  L  H  I  F  L
           P  K  L  H  D  F  Q  Q  W  L  I  A  V  H  S  S  I  F  S  S
    601  CCAAAGCTTCATGATTTTCAGCAATGGTTAATAGCTGTACATTCCTCCATATTTTCCTCT
           C  C  S  F  L  Y  S  F  C  C  A  V  V  A  G  S  N  T  T  Y
           V  A  A  S  C  T  L  F  V  V  L  W  L  R  V  P  I  L  R  T
    661  GTTGCAGCTTCTTGTACTCTTTTTGTTGTGCTGTGGTTGCGGGTTCCAATACTACGTACT
           C  F  W  F  P  L  V  R  G  N  F  S  F  E  L  T  V  N  Y  T
           V  F  G  F  R  W  L  G  A  I  F  L  S  N  S  Q  *
    721  GTTTTTGGTTTCCGCTGGTTAGGGGCAATTTTTCTTTCGAACTCACAGTGAATTACACGG
           V  C  P  P  C  L  T  R  Q  A  A  T  E  I  Y  E  P  G  R  S
    781  TGTGTCCACCTTGCCTCACCCGGCAAGCAGCCACAGAGATCTACGAACCCGGTAGGTCTC
           L  W  C  R  I  G  Y  D  R  C  G  E  D  D  H  D  E  L  G  F
    841  TTTGGTGCAGGATAGGGTATGACCGATGTGGGGAGGACGATCATGACGAGCTAGGGTTTA
           M  I  P  P  G  L  S  S  E  G  H  L  T  G  V  Y  A  W  L  A
    901  TGATACCGCCTGGCCTCTCCAGCGAAGGCCACTTGACTGGTGTTTACGCCTGGTTGGCGT
           F  L  S  F  S  Y  T  A  Q  F  H  P  E  I  F  G  I  G  N  V
    961  TCTTGTCCTTCAGCTACACGGCCCAGTTCCATCCCGAGATATTCGGGATAGGGAATGTGA
           S  R  V  Y  V  D  I  K  H  Q  L  I  C  A  E  H  D  G  Q  N
   1021  GTCGAGTTTATGTTGACATCAAACATCAACTCATCTGCGCCGAACATGACGGGCAGAACA
```

Fig. 2B.

```
              T  T  L  P  R  H  D  N  I  S  A  V  F  Q  T  Y  Y  Q  H  Q
       1081  CCACCTTGCCTCGTCATGACAACATTTCAGCCGTGTTTCAGACCTATTACCAACATCAAG
ORF 4                                           M  A  S  S  L  L  F  L  V  V  G
              V  D  G  G  N  W  F  H  L  E  W  L  R  P  F  F  S  S  W  L
       1141  TCGACGGCGGCAATTGGTTTCACCTAGAATGGCTTCGTCCCTTCTTTTCCTCGTGGTTGG
                 F  K  C  L  L  V  S  Q  A  F  A  C  K  P  C  F  S  S  S  L
              V  L  N  V  S  W  F  L  R  R  S  P  A  N  H  V  S  V  R  V
       1201  TTTTAAATGTCTCTTGGTTTCTCAGGCGTTCGCCTGCAAACCATGTTTCAGTTCGAGTCT
                 A  D  I  K  T  N  T  T  A  A  A  S  F  A  V  L  Q  D  I  S
              L  Q  I  L  R  P  T  P  P  Q  R  G  A  L  L  S  S  K  T  S
       1261  TGCAGATATTAAGACCAACACCACCGCAGCGGCAAGCTTTGCTGTCCTCCAAGACATCAG
                 C  L  R  H  R  D  S  A  S  E  A  I  R  K  I  P  Q  C  R  T
              V  A  L  G  I  A  T  R  P  L  R  R  F  A  K  S  L  S  A  V
       1321  TTGCCTTAGGCATCGCGACTCGGCCTCTGAGGCGATTCGCAAAATCCCTCAGTGCCGTAC
                 A  I  G  T  P  V  Y  V  T  I  T  A  N  V  T  D  E  N  Y  L
              R  R  *
       1381  GGCGATAGGGACACCCGTGTATGTTACCATCACAGCCAATGTGACAGATGAGAATTATTT
                 H  S  S  D  L  L  M  L  S  S  C  L  F  Y  A  S  E  M  S  E
       1441  ACATTCTTCTGATCTCCTCATGCTTTCTTCTTGCCTTTTCTATGCTTCTGAGATGAGTGA
                 K  G  F  K  V  V  F  G  N  V  S  G  I  V  A  V  C  V  N  F
       1501  AAAGGGATTTAAGGTGGTATTTGGCAATGTGTCAGGCATCGTGGCTGTGTGTGTCAATTT
                 T  S  Y  V  Q  H  V  K  E  F  T  Q  R  S  L  V  V  D  H  V
       1561  TACCAGCTACGTCCAACATGTCAAGGAGTTTACCCAACGCTCCCTGGTGGTCGACCATGT
                 R  L  L  H  F  M  T  P  E  T  M  R  W  A  T  V  L  A  C  L
       1621  GCGGTTGCTCCATTTCATGACACCTGAGACCATGAGGTGGGCAACTGTTTTAGCCTGTCT
ORF 5            F  A  I  L  L  A  I  *              M  L  E  K  C  L  T  A
       1681  TTTTGCCATTCTGTTGGCAATTTGAATGTTTAAGTATGTTGGAGAAATGCTTGACCGCGG
                 G  C  C  S  R  L  L  S  L  W  C  I  V  P  F  C  F  A  V  L
       1741  GCTGTTGCTCGCGATTGCTTTCTTTGTGGTGTATCGTGCCGTTCTGTTTTGCTGTGCTCG
                 A  N  A  S  N  D  S  S  S  H  L  G  L  I  Y  N  L  T  L  C
       1801  CCAACGCCAGCAACGACAGCAGCTCCCATCTACAGCTGATTTACAACTTGACGCTATGTG
                 E  L  N  G  T  D  W  L  A  N  K  F  D  W  A  V  E  S  F  V
       1861  AGCTGAATGGCACAGATTGGCTAGCTAACAAATTTGATTGGGCAGTGGAGAGTTTTGTCA
                 I  F  P  V  L  T  H  I  V  S  Y  G  A  L  T  T  S  H  F  L
       1921  TCTTTCCCGTTTTGACTCACATTGTCTCCTATGGTGCCCTCACTACCAGCCATTTCCTTG
                 D  T  V  A  L  V  T  V  S  T  A  G  F  V  H  G  R  Y  V  L
       1981  ACACAGTCGCTTTAGTCACTGTGTCTACCGCCGGGTTTGTTCACGGGCGGTATGTCCTAA
                 S  S  I  Y  A  V  C  A  L  A  A  L  T  C  F  V  I  R  F  A
       2041  GTAGCATCTACGCGGTCTGTGCCCTGGCTGCGTTGACTTGCTTCGTCATTAGGTTTGCAA
```

Fig. 2C.

```
               K  N  C  M  S  W  R  Y  A  C  T  R  Y  T  N  F  L  L  D  T
       2101   AGAATTGCATGTCCTGGCGCTACGCGTGTACCAGATATACCAACTTTCTTCTGGACACTA
                K  G  R  L  Y  R  W  R  S  P  V  I  I  E  K  R  G  K  V  E
       2116   AGGGCAGACTCTATCGTTGGCGGTCGCCTGTCATCATAGAGAAAAGGGGCAAAGTTGAGG
                V  E  G  H  L  I  D  L  K  R  V  V  L  D  G  S  V  A  T  P
       2221   TCGAAGGTCATCTGATCGACCTCAAAAGAGTTGTGCTTGATGGTTCCGTGGCAACCCCTA
ORF 6                                          M  G  S  S  L  D  D  F  C  H  D  S  T
                I  T  R  V  S  A  E  Q  W  G  R  P  *
       2281   TAACCAGAGTTTCAGCGGAACAATGGGGTCGTCCTTAGATGACTTCTGTCATGATAGCAC
                A  P  Q  K  V  L  L  A  F  S  I  T  Y  T  P  V  M  I  Y  A
       2341   GGCTCCACAAAAGGTGCTTTTGGCGTTTTCTATTACCTACACGCCAGTGATGATATATGC
                L  K  V  S  R  G  R  L  L  G  L  L  H  L  L  I  F  L  N  C
       2401   CCTAAAGGTGAGTCGCGGCCGACTGCTAGGGCTTCTGCACCTTTTGATCTTCCTGAATTG
                A  F  T  F  G  Y  M  T  F  A  H  F  Q  S  T  N  K  V  A  L
       2461   TGCTTTCACCTTCGGGTACATGACTTTCGCGCACTTTCAGAGTACAAATAAGGTCGCGCT
                T  M  G  A  V  V  A  L  L  W  G  V  Y  S  A  I  E  T  W  K
       2521   CACTATGGGAGCAGTAGTTGCACTCCTTTGGGGGGTGTACTCAGCCATAGAAACCTGGAA
                F  I  T  S  R  C  R  L  C  L  L  G  R  K  Y  I  L  A  P  A
       2581   ATTCATCACCTCCAGATGCCGTTTGTGCTTGCTAGGCCGCAAGTACATTCTGGCCCCTGC
                H  H  V  E  S  A  A  R  F  H  P  I  A  A  N  D  N  H  A  F
       2641   CCACCACGTTGAAAGTGCCGCACGGTTTCATCCGATTGCGGCAAATGATAACCACGCATT
                V  V  R  R  P  G  S  T  T  V  N  G  T  L  V  P  G  L  K  S
       2701   TGTCGTCCGGCGTCCCGGCTCCACTACGGTCAACGGCACATTGGTGCCCGGGTTAAAAAG
ORF 7                                                                              M
                L  V  L  G  G  R  K  A  V  K  Q  G  V  V  N  L  V  K  Y  A
       2761   CCTCGTGTTGGGTGGCAGAAAAGCTGTTAAACAGGGAGTGGTAAACCTTGTCAAATATGC
                P  N  N  N  G  K  Q  T  E  E  K  K  G  D  G  Q  P  V  N  Q
                K  *
       2821   CAAATAACAACGGCAAGCAGACAGAAGAGAAGAAGGGGGATGGCCAGCCAGTCAATCAGC
                L  C  Q  M  L  G  K  I  I  A  Q  Q  N  Q  S  R  G  K  G  P
       2881   TGTGCCAGATGCTGGGTAAGATCATCGCTCAGCAAAACCAGTCCAGAGGCAAGGGACCGG
                G  K  K  N  K  K  K  N  P  E  K  P  H  F  P  L  A  T  E  D
       2941   GAAAGAAAAATAAGAAGAAAAACCCGGAGAAGCCCCATTTTCCTCTAGCGACTGAAGATG
                D  V  R  H  H  F  T  P  S  E  R  Q  L  C  L  S  S  I  Q  T
       3001   ATGTCAGACATCACTTTACCCCTAGTGAGCGGCAATTGTGTCTGTCGTCAATCCAGACCG
                A  F  N  Q  G  A  G  T  C  T  L  S  D  S  G  R  I  S  Y  T
       3061   CCTTTAATCAAGGCGCTGGGACTTGCACCCTGTCAGATTCAGGGAGGATAAGTTACACTG
```

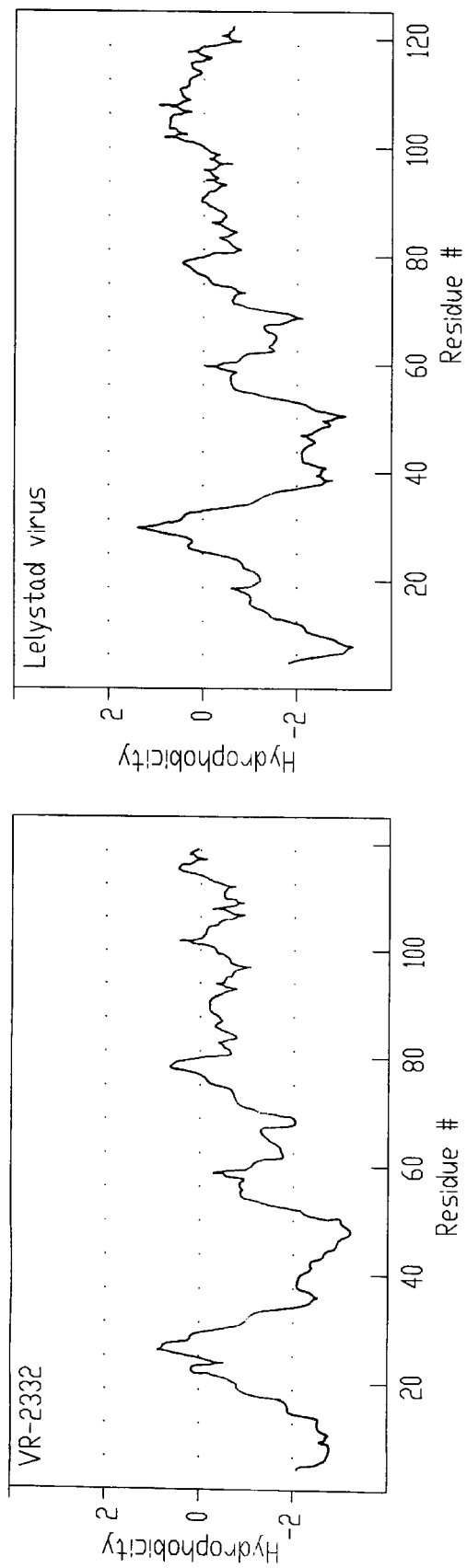

```
2332   1  MGssLDDFChDstApQKvlLAFSITYTPvMIYALKVSRGRLLGLLHlLIFLNCaFTFGYMTfaHFQSTNkVA
LV     1  MG-gLDDFCnDpiAaQKlvLAFSITYTPiMIYALKVSRGRLLGLLHiLIFLNCsFTFGYMTyvHFQSTNrVA

73  LTmGAVVALLWGVYSaiEtWKFITSRCRLCl LGRkYILAPAHHVESAArfHpIaAndNhAfvVRrPGsTtVN
      72  LTl GAVVALLWGVYSftEsWKFITSRCRLCcLGRrYILAPAHHVESAAglHsIsAsgNrAyaVRkPGlTsVN

145  GTLVPGLkSLVLGGrkAVKqGVVNLVKYak
     144  GTLVPGLrSLVLGGkrAVKrGVVNLVKYgr

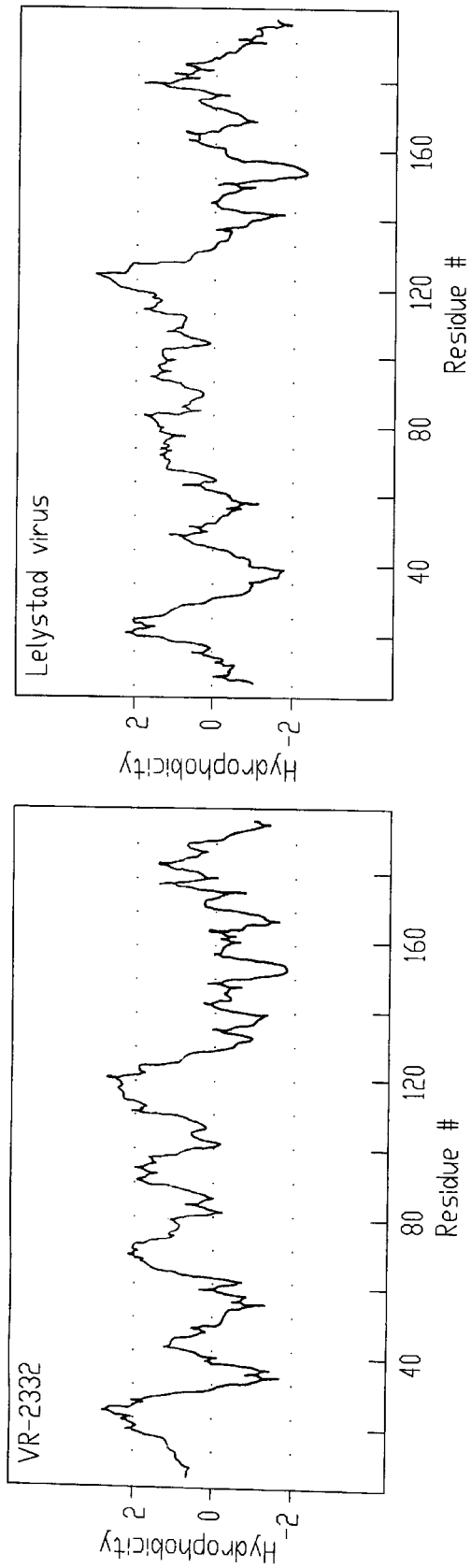

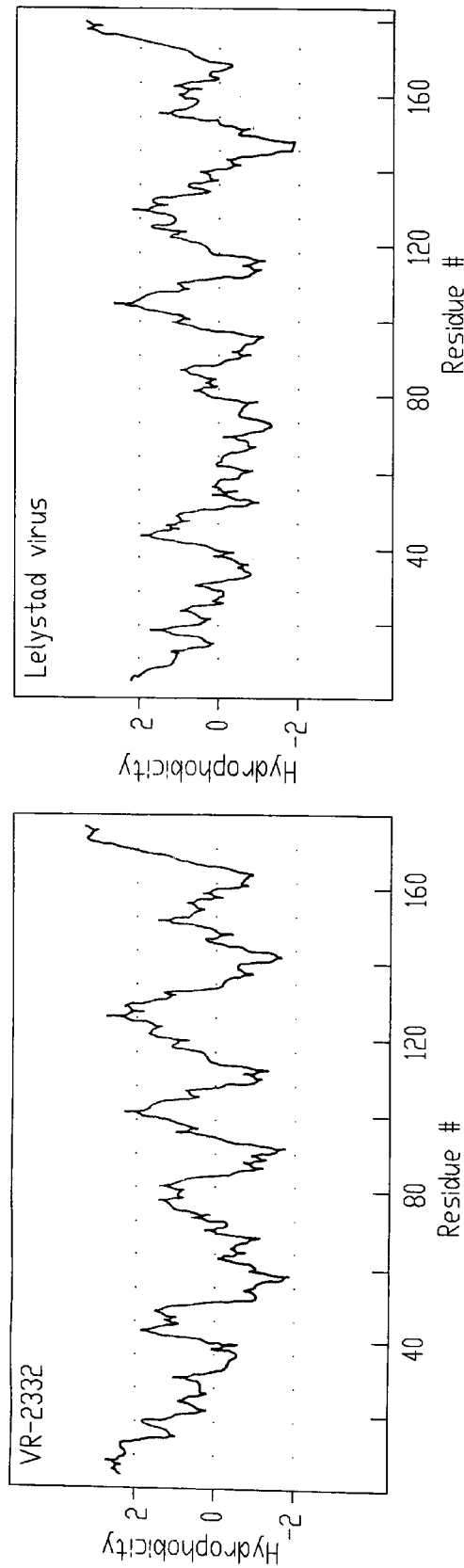

Fig. 7A.

```
2332    1  MvnsCtflHiFLCcsflYsfccAvvagSntTyCFWFPLvrGNsFFELTvNYTvCpPCITrQAAteiyEPGRs
            |  |||||| ||| |||  |  |  ||||||||||||||| ||| ||||  | ||||     |||||
LV      1  MahqCarfHfFLCgficYlvhsAlasnSssTlCFWFPLahFNtSFELTiNYTiCmPCsTsQAArqrlEPGRn 73  tWCrIGyDRCgEdDHDELgfmIPpGIsseghLtGvYAWLAFLSFSYtAQFHPEiFGIGNVSRVyVDikHQlI
            ||| ||||| | ||||||  |||  |     ||||||||||||| |||||||||||||||||  | |||
       73  mWCkIGhDRCeErDHDELlmsIPsG-ydnlkLeGyYAWLAFLSFSYaAQFHPElFGIGNVSRVfVDkrHQfI 145  CAEHDGqNtTlprhdNISAvfqtYYqhHQvDGGNWFHLEWLRPfFSSWLVLNvSWFLRRSPanhVSvRvIQIL
            |||||| |  |   |||| |  || ||  ||||||||||||| |||||||| ||||||||||  ||  |||
      144  CAEHDGhNsTvstghNISAlyaaYYhHQiDGGNWFHLEWLRPlFSSWLVLNiSWFLRRSPvspVSrRiyQIL 217  RPTpPqrqal SskTS-V-aL-G--iatR--P--lR-rfaK-S-LsavrR
            |||  |  |   | ||  |  |    ||  |  ||  | | | |
      216  RPTrPrlpvswSfrTSiVsdLtGsqqrkRKfPsesRpnvvKpSvLpstsR
```

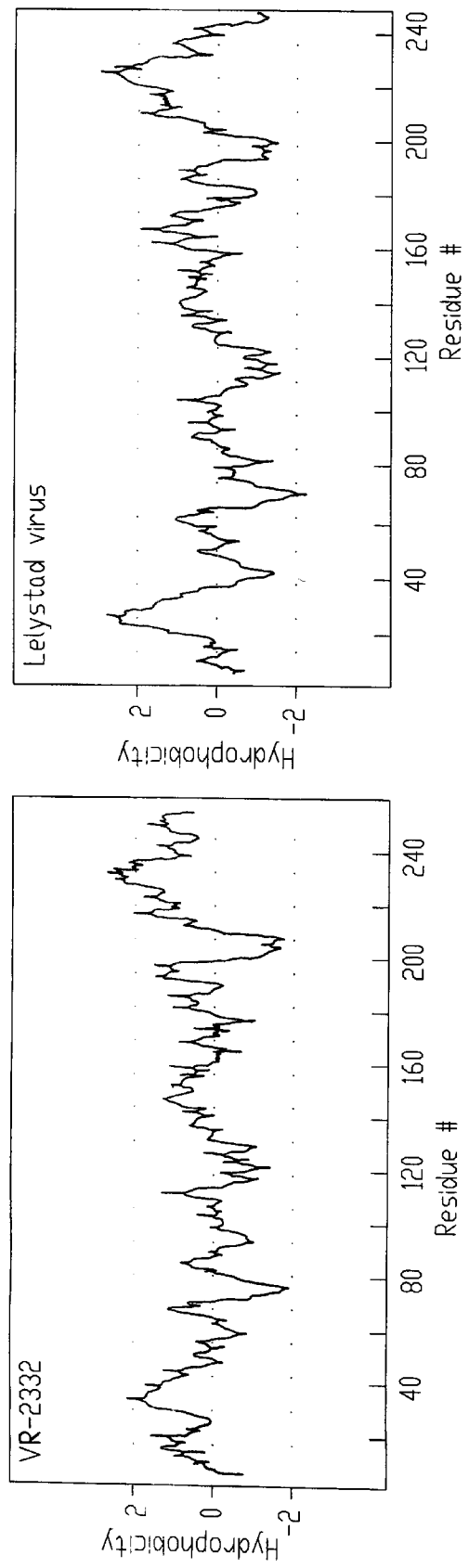

```
VR-2332    1  TGGGCTGGCATTCTTGAGGCATCTCAGTGTTGTTGAATTGGAAGAATGTGTGGTGAATGGCAC
                                          ||  ||  ||||||||| ||  ||  ||||||||
LV         1                              ATTTGACAGTCAGGTGAATGGCCG

VR-2332   62  TGATTGACATTGTGCCTCTAAGTCACCTATTCAATTAGGGCGACCGTGTGGGGTGAGATT
              |||||  |||  |  ||||| |||||||||||||||||  |||||  |||||| ||   
LV        25  CGATTGGCGTGTGGCCTCTGAGTCACCTATTCAATTAGGGCGATCACATGGGGTCATACT

VR-2332  123  TAAT TGGCGAGAACCATGCGGCCCGAAATTAAAAAAAAAAAAAAAAAAAAAAAA
              ||||  ||  ||  |||||||| ||||||| |||||||||||||||||||||||
LV        86  TAATCAGGCAGGAACCATGTGACCGAAATTAAAAAAAAAAAAAAAAAAAAAAAA
```

Fig. 9.

VR-2332 VIRAL NUCLEOTIDE SEQUENCE AND METHODS OF USE

This application is a continuation of application number 08/287,941 filed Aug. 5, 1994, now abandoned.

Sequence Listing

A printed Sequence Listing accompanies this application, and is also submitted with identical contents in the form of a computer-readable ASCII file.

BACKGROUND OF THE INVENTION

1. Field of the Invention

The invention pertains to the field of molecular genetics and, in particular, to the use of man-made nucleotides in diagnosing animal diseases or vaccinating animals against disease. More specifically, the preferred nucleotides derive from an immunologically distinct strain of the porcine reproductive and respiratory syndrome ("PRRS") virus, and selectively target this virus in the application of vaccination or diagnostic techniques.

2. Description of the Prior Art

A new viral disease of pigs was detected in North America during 1987, and reported by Hill, *Overview and History of Mystery Swine Disease (Swine Infertility and Respiratory syndrome)*, in Proceedings of the Mystery Swine Disease Committee Meeting, October 6, Denver Colo., from the Livestock Conservation Institute of Madison, Wis. pp. 29–30 (1990). A disease having substantially identical clinical signs was found in Europe during 1990, as reported by Paton et al., *Blue ear disease of pigs*, 128 Vet Rec. 617 (1991). The clinically observed disease is commonly known by various names including porcine reproductive and respiratory syndrome ("PRRS"), swine infertility and respiratory syndrome ("SIRS"), porcine epidemic abortion and respiratory syndrome ("PEARS"), and mystery swine disease; herein, the term PRRS will suffice to indicate all of these names.

The consequences of this disease included late-term abortions and stillbirths in sows, as well as respiratory insufficiencies in nursery pigs that developed poorly and died easily. Decreases were observed in sow conception rates and litter sizes. Estimates stated that about ten to fifteen percent of pig production were lost annually due to reproductive failure. Early clinical signs of the disease included anorexia and mild pyrexia. Other signs included bluish discolorations on the skin of diseased herd animals, with the discolorations being primarily located on the ears, teats, snout, and frontal portions of the neck and shoulders. Necropsy results indicated thickened alveolar septae caused by the presence of macrophages, degenerating cells, and debris in alveolar spaces. These abnormalities indicated the presence of PRRS virus.

The causative viral agent was suspected to be a small, enveloped positive-stranded RNA virus that was recovered primarily from alveolar macrophages of infected swine, as reported by Benfield et al., *Characterization of swine infertility and respiratory syndrome (SIRS) virus (isolate ATCC VR-2332)*, 4 J. Vet. Diagn. Invest. 127–133 (1992); and Wensvoort et al., *Lelystad virus, the cause of porcine epidemic abortion and respiratory syndrome: a review of mystery swine disease research at Lelystad*, 33 Vet. Micro. 185–193 (1992). The isolation technique for the Lelystad ("LV") virus included homogenizing infected swine lung tissue; mixing the homogenate with a physiological saline, e.g., Ringers solution, Hank's balanced salt solution, and Minimum Essential Medium ("MEM") to a 10% weight/volume amount of the homogenate; and filtering the mixture through a series of 0.45, 0.2 and 0.1 micron filters.

The LV virus appeared to be closely related to arteriviruses in morphology, genome organization, transcriptional regulation, and macrophage specificity, according to Plagemann et al., *Lactate dehydrogenase-elevating virus, equine arteritis virus and simian hemorrhagic fever virus: a new group of positive-strand RNA viruses*, 41 Adv. Vir. Res. 99–192 (1992).

The complete nucleotide sequence of the LV strain of the PRRS virus was identified by Meulenberg et al., *Lelystad virus, the causative agent of porcine epidemic abortion and respiratory syndrome (PEARS), is related to LDV and EAV*, 192 Virology 62–72 (1993). A partial LV sequence was also identified by Conzelmann et al., *Molecular characterization of porcine reproductive and respiratory syndrome virus, a member of the arterivirus group*, 193 Virology 193, 329–339. The positive-strand genome of the LV virus (Sequence ID. Nos. 14–26) included eight open reading frames ("ORFs"), which had some similarity in comparison with the genes of coronaviruses and arteriviruses. Two open reading frames likely coded for the viral RNA polymerase. LV ORFs two through six appeared to code for structural proteins associated with viral membranes, and LV ORF 7 was believed to code for a nucleocapsid.

The LV viral proteins were expressed from a nested set of RNA transcripts that had overlapping 3' ends. While this expression strategy was shared with the Coronavirus family, the physical properties of the LV virus originally placed it in the Togavirus family. Plagemann et al. (see above) has proposed a new family, the Arteriviridae, to encompass viruses having these dual properties. This family included the PRRS virus, equine arteritis virus ("EAV"), lactate dehydrogenase-elevating virus ("LDV"), and simian hemorrhagic fever virus ("SHFV").

A second strain ("VR-2332") of the PRRS virus was isolated as a fourth cell culture passage, as reported by Benfield et al., *Characterization of swine infertility and respiratory syndrome* (*SIRS*) *virus* (*isolate ATCC VR*-2332), 4 J. Vet. Diagn. Invest. 4, 127–133 (1992). Nevertheless, the viral genome was not sequenced. The VR2332 isolate was deposited in the American Type Culture Collection, and now has an ATCC catalogue number VR-2332. The VR-2332 virus was characterized as spherical with an average diameter of 62 nm and a 25–30 nm core surrounded by an envelope. Viral particles had a buoyant density of 1.18–1.19 g/ml in cesium chloride and were further purified from filtered tissue homogenates by centrifugation on cesium chloride gradients.

The respective VR-2332 and LV virus isolates displayed vast differences in terms of antigenic variation, especially in view of their common morphology and similar clinical signs in swine. A comparison study between 24 field sera and seven viral isolates from Europe and North America failed to distinguish a single common antigen which was able to diagnose infection in a reliable manner for both viruses, as reported by Wensvoort et al., *Antigenic comparison of Lelystad virus and swine infertility and respiratory syndrome* (*SIRS*) *virus,* 4 J. Vet. Diagn. Invest. 134–138 (1992). Accordingly, despite the structural and symptomological similarities between the two virus strains, it is unlikely that a single vaccine could be developed from one strain of the virus for purposes of immunizing swine against both strains.

SUMMARY OF THE INVENTION

The present invention overcomes the problems that are outlined above by providing man-made nucleotide sequences for the immunologically distinct VR-2332 strain of PRRS virus, as well as vaccines derived from these nucleotides and corresponding methods of vaccination.

Broadly speaking, the present invention includes materials and methods that derive from the VR-2332 form of PRRS pathogen. The materials preferably include VR-2332 virus based nucleic acids and proteins having lengths sufficient to make them unique in comparison with the LV form of PRRS pathogen. The methods involve the use of these materials in diagnostic assays and vaccination procedures.

A particularly preferred material of the present invention includes a purified and isolated nucleic acid coding for a fragmentary portion of the VR-2332 genomic sequence between ORF 2 and ORF 7. These sequences are unique with respect to the LV virus genome, and preferably code for the expression of a polypeptide capable of inducing an anti-VR-2332 PRRS immune response in swine. Despite the similarity in PRRS clinical signs and viral morphology between the VR-2332 and LV viruses, VR-2332 based oligonucleotides can be used as polymerase chain reaction ("PCR") primers for the selective amplification of VR-2332 cDNA. These sequences also include inverse complimentary oligonucleotide sequences derived from the VR-2332 genome. These oligonucleotide sequences are also capable of being used as probes in hybridization studies to selectively identify wild-type VR-2332 cDNA.

Portions of the VR-2332 nucleotide sequence may be recombined with a chimeric vector to place the VR-2332 coding region insert under the control of an appropriate promoter sequence and a termination sequence. This vector may be used for host expression of a protein coded for by the insert. Host expression may be accomplished in either prokaryotic or eukaryotic cells. These vectors may be constructed as recombinant plasmids and injected directly into swine to induce an immune response as the host-swine produces viral proteins. Alternatively, the viral proteins may be produced in cell cultures and injected into swine for immunization purposes.

These nucleotide sequences may also be used in PCR diagnostic assays utilizing primers that selectively amplify either VR-2332-based cDNA or LV-based cDNA. Alternatively, these primer sequences can be used in hybridization reactions that indicate the presence of a particular PRRS-causative virus.

Other objects, advantages and salient features of the present invention will become apparent from the following detailed description which, when taken into conjunction with the annexed drawings, discloses a number of embodiments of the present invention.

BRIEF DESCRIPTION OF THE DRAWINGS

FIG. 2 depicts the nucleotide and deduced amino acid sequence of VR-2332 ORFs 2 through 7, which correspond to Sequence ID Nos. 1 through 13;

FIG. 3A depicts a comparison between the respective amino acid alignments of ORF 7 for VR-2332 and LV virus according to an IUPAC single letter amino acid code wherein identical residues are represented by capital letters and different residues are represented by lower case letters, and the full three letter amino acid code sequences for these residues are provided in Sequence ID No. 13 (VR-2332) and Sequence ID. No. 26 (LV virus);

FIG. 3B depicts a hydropathy profile for VR-2332 ORF 7, wherein the ordinate represents a hydrophobicity value and the abscissa represents a residue number;

FIG. 3C depicts a hydropathy profile for LV virus ORF 7, which is substantially similar to FIG. 3B;

FIG. 4A depicts a comparison between the respective amino acid alignments of ORF 6 for VR-2332 and LV virus according to an IUPAC single letter amino acid code wherein identical residues are represented by capital letters and different residues are represented by lower case letters, and the full three letter amino acid code sequences for these residues are provided in Sequence ID No. 11 (VR-2332) and Sequence ID. No. 24 (LV virus);

FIG. 4B depicts a hydropathy profile for VR-2332 ORF 6, wherein the ordinate represents a hydrophobicity value and the abscissa represents a residue number;

FIG. 4C depicts a hydropathy profile for LV virus ORF 6, which is substantially similar to FIG. 4B;

FIG. 5A depicts a comparison between the respective amino acid alignments of ORF 5 for VR-2332 and LV virus according to an IUPAC single letter amino acid code wherein identical residues are represented by capital letters and different residues are represented by lower case letters, and the full three letter amino acid code sequences for these residues are provided in Sequence ID No. 9 (VR-2332) and Sequence ID. No. 22 (LV virus);

FIG. 5B depicts a hydropathy profile for VR-2332 ORF 5, wherein the ordinate represents a hydrophobicity value and the abscissa represents a residue number;

FIG. 5C depicts a hydropathy profile for LV virus ORF 5, which is substantially similar to FIG. 5B;

FIG. 6A depicts a comparison between the respective amino acid alignments of ORF 4 for VR-2332 and LV virus according to an IUPAC single letter amino acid code wherein identical residues are represented by capital letters and different residues are represented by lower case letters, and the full three letter amino acid code sequences for these residues are provided in Sequence ID No. 7 (VR-2332) and Sequence ID. No. 20 (LV virus);

FIG. 6B depicts a hydropathy profile for VR-2332 ORF 4, wherein the ordinate represents a hydrophobicity value and the abscissa represents a residue number;

FIG. 6C depicts a hydropathy profile for LV virus ORF 4, which is substantially similar to FIG. 6B;

FIG. 7A depicts a comparison between the respective amino acid alignments of ORF 3 for VR-2332 and LV virus according to an IUPAC single letter amino acid code wherein identical residues are represented by capital letters and different residues are represented by lower case letters, and the full three letter amino acid code sequences for these residues are provided in Sequence ID No. 5 (VR-2332) and Sequence ID. No. 18 (LV virus);

FIG. 7B depicts a hydropathy profile for VR-2332 ORF 3, wherein the ordinate represents a hydrophobicity value and the abscissa represents a residue number;

FIG. 7C depicts a hydropathy profile for LV virus ORF 3, which is substantially similar to FIG. 7B;

FIG. 8A depicts a comparison between the respective amino acid alignments of ORF 2 for VR-2332 and LV virus according to an IUPAC single letter amino acid code wherein identical residues are represented by capital letters and different residues are represented by lower case letters, and the full three letter amino acid code sequences for these residues are provided in sequence ID No. 3 (VR-2332) and Sequence ID. No. 16 (LV virus);

FIG. 8B depicts a hydropathy profile for VR-2332 ORF 2, wherein the ordinate represents a hydrophobicity value and the abscissa represents a residue number;

FIG. 8C depicts a hydropathy profile for LV virus ORF 2, which is substantially similar to FIG. 8B; and FIG. 9 depicts a comparison between the respective 3' untranslated regions of VR-2332 (sequence ID NO. 24) and LV virus (sequence ID NO. 35).

DETAILED DESCRIPTION OF THE PREFERRED EMBODIMENT

Figures 1, 2D:
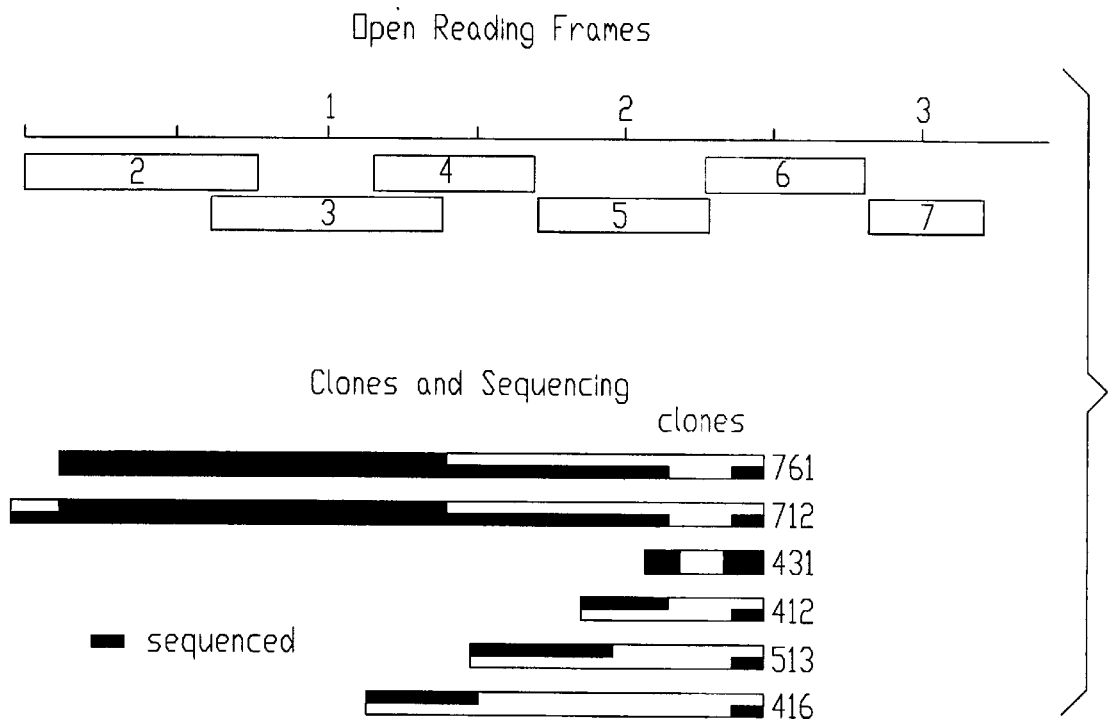
FIG. 1 depicts the positional organization of VR-2332 ORFs 2 through 7 with reference to shaded regions corresponding to cDNA fragments from various clones that were used to determine the nucleotide sequence of the VR-2332 strain of the PRRS virus to yield Sequence ID No. 1.

The following non-limiting Examples set forth preferred methods and materials for practicing the present invention.

EXAMPLE 1

Growth of the VR-2332 Virus

A virally pure MA-104 cell line culture of the ATCC VR-2332 virus was obtained for use as viral inoculum, courtesy of Boehringer Ingelheim of Ridgefield, Conn.

A culture was prepared for use in propagating the VR-2332 inoculum. The VR-2332 virus was grown in cells from a monkey kidney cell line according to the methods outlined by Gravell et al., 181 Proc. Soc. Exp. Biol. Med., 112–119. Those skilled in the art may alternatively refer to the cell line as the 2621, MA-104 or USU-104 cell line. Uninfected cells were cultured in 50 ml of Eagle's MEM medium (purchased from Life Technologies, Inc., Gaithersburg, Md.), which was supplemented with 10% fetal calf serum and 50 $\mu$g/ml gentamicin from Sigma Chemical Co. of St. Louis, Mo. Cells were dislodged from the flask surface with trypsin-versene, centrifuged to pellet the cells for separation from the trypsin-versene supernatant, and split 1:4 for subculturing. The cells were maintained in a 5% humidified $CO_2$ atmosphere at 37° C. in 75 $cm^2$ plastic tissue culture flasks, with media passage at 5–7 day intervals.

The four 50 ml cell cultures were each infected by decanting the growth media and adding the VR-2332 inoculum in 1 ml of growth media having a titer of approximately $10^5$–$10^6$ tissue culture infective doses ($TCID_{50}$). The resultant mixture was incubated for 30 min, after which time was added 30 ml of fresh MEM media containing 4% fetal calf serum. The infected cells were incubated under $CO_2$ as described above for 24 or 48 hr, and harvested by decanting the media to leave cells adhered to the flask walls.

EXAMPLE 2

Construction of a cDNA Library

The harvested cells from Example 1 were washed with phosphate-buffered saline, and lysed by the addition of 5M guanidine isothiocyanate. Total cellular RNA was extracted according to the protocols described by Chomczynski et al., Single-step method of RNA isolation by acid guanidinium thiocyanate-phenol-chloroform extraction, 162 Anal. Biochem. 156–159 (1987). Poly A-containing RNA was selected by oligo dT column chromatography using conventional equipment and procedures from Gibco BRL of Gaithersburg, Md.

A cDNA library was constructed in the lambda unidirectional phage vector, UniZap™XR, using Gigapack® II Gold[1] packaging extract and E. coli SURE™ cells, as directed by the kit manufacturer (Stratagene, La Jolla, Calif.). This procedure is summarized below with reference to materials provided in the commercially available kit.

The poly A-selected RNA obtained from 2 ml of cell lysate was reverse transcribed with Moloney murine leukemia virus reverse transcriptase and a synthetic

[1]UniZap XR, Gigapack II Gold, and SURE are trademarks of Stratagene Corp. of La Jolla, Calif. base oligo dT primer containing a sequence (sequence ID NO. 27) including an Xho I restriction site, as follows:

5'-GAGAGAGAGAGAGAGAGAGAACTAGTCTCGA-GTTTTTTTTTTTTTTTTTT-3'.

The first strand synthesis reaction also contained 5-methyl dCTP. Second strand synthesis was achieved by utilizing DNA polymerase I and the standard dCTP instead of 5-methyl dCTP. The ends of the double stranded cDNA were made blunt with T4 DNA polymerase, and EcoRI adaptors were added with T4 DNA ligase. The adaptors had the following synthetic nucleotide sequences:
5'-AATTCGGCACGAG-3' (sequence ID NO. 28)
3'-GCCGTGCTC-5' (sequence ID NO. 29)

The resulting cDNA was treated with polynucleotide kinase to phosphorlate the 5' ends, digested to completion with Xho I, and purified on a Sephacryl S-400 column.

The cDNA was ligated to the Uni-ZAP™ XR vector arms with DNA ligase and packaged in the high efficiency packaging extract, Gigapack® II Gold. The resulting packaged infectious phage preparation was plated on the E. coli cell line SURE™.

EXAMPLE 3

Screening the cDNA Library by PCR

Many unsuccessful attempts were made to screen the cDNA library of Example 2 for purposes of identifying VR-2332 positive plaques by polymerase chain reaction using PCR primer sequences derived from the reported LV virus. Synthetic DNA fragments or primers were produced and labeled with $^{32}$p as an indicator according to conventional protocols. These oligonucleotide primers replicated portions of LV virus ORFs 2, 6 and 7, as were reported by Meulenberg et al., Lelystad virus, the causative agent of porcine epidemic abortion and respiratory syndrome (PEARS), is related to LDV and EAV, 192 Virology 62–72 (1993). No PCR amplified nucleotide products were obtained under a variety of conditions.

The observed total failure in PCR amplification of VR-2332 nucleic acid sequences indicated that the two viruses (LV and VR-2332) have considerable nucleotide sequence differences, which are sufficient to prevent specific PCR amplification of VR-2332 cDNA using LV-derived primers. Therefore, an alternative cloning strategy was devised using LV sequences for hybridization, but not for PCR, to determine the nucleotide sequence corresponding to the structural genes of the VR-2332 strain of the PRRS virus.

EXAMPLE 4

Screening the cDNA Library by Plaque Hybridization

A PCR-generated nucleotide fragment that replicated cDNA from LV ORF 7 (Sequence ID No. 26 of the LV virus) was $^{32}$P-labeled, and used to probe Northern blots obtained using MA-104 cells infected with the VR-2332 virus. Radiographic bands were obtained from infected cells, but not from uninfected cells. These bands indicated that LV and VR-2332 shared similar sequences which were capable of hybridizing despite the failure of PCR screening in Example 3.

Several fifteen cm agar plates containing a total of about 50,000 plaques were screened from duplicate lifts onto NitroPlus nitrocellulose membranes (Micron Separations Inc., Westboro, Mass.). Positive plaques that hybridized to the corresponding LV virus probe were identified by their corresponding radiographic bands as determined by exposure to x-ray film. These positive plaques were replated and rescreened for confirmation. Hybridization-positive recombinant Uni-ZAP™ XR phage were subjected to in vivo excision as described in the Stratagene instruction manual, in order to obtain plasmid DNA for sequence analysis. A summary of the Stratagene procedure is set forth below.

Recombinant phage were combined with *E. coli* XL1-Blue cells as well as ExAssist helper phage at 37° C. for 15 min and, thereafter, cultured in rich media for 2–3 hours with shaking at 37° C. The culture was heated to 70° C. for 20 min, and clarified by centrifugation. Supernatant containing rescued phagemid was added to SOLR cells and plated on ampicillin-containing agar plates. These bacterial colonies contained recombinant plasmids.

The resultant clones were amplified in liquid culture. DNA was extracted and further analyzed by EcoRI and XhoI restriction endonuclease digestion (10X excess). The sizes of the VR-2332-specific inserts were estimated by electrophoresis in agarose gels with molecular weight standards. Next, the nucleotide sequence of 23 clones was determined at the 3' end by dideoxynucleotide sequencing using Sequenase, $^{35}$S-dATP and Stratagene's synthetic M13-20 primer:
5'-GTAAAACGACGGCCAGT-3' (sequence ID NO. 30)
Sequencing products were analyzed on 6% denaturing polyacrylamide gels. Twenty of 23 clones had identical 3' sequences, suggesting these clones were coterminally nested. Six of these 20 clones of various sizes, all containing an identical 3' end, were selected for further DNA sequencing.

EXAMPLE 5

VR-2332 Sequence Analysis

Nucleotide sequence data were obtained for each of the six selected clones of Example 4 by manual dideoxynucleotide sequencing with Sequenase (US Biochemicals, Cleveland, Ohio) and automated fluorescence sequencing (Applied Biosystems, Foster City, Calif.).

FIG. 1 schematically depicts the native positions of the six clones, i.e., those designated 761, 712, 431, 412, 513, and 416, which were chosen for further sequence analysis. The fragment length scale proceeds from 0 to about 3.5 kb, with a positional reference to Sequence ID No. 1. Clones 431, 412, 513 and 416 were sequenced from their 5' ends to overlap with the sequence generated from the next smaller clone. The gap between the 5' end of clone 416 and the beginning of ORF 2, which was sequenced from both clones 712 and 761, was sequenced from both ends by synthesizing VR-2332-specific primers. Additional sequencing was performed to confirm the sequence on the opposite strand. This strategy produced a sequence of 3358 nucleotides, i.e., Sequence ID. No. 1, on both strands from a combination of six independent clones. FIG. 2 depicts this total sequence, together with its deduced amino acid translation.

Numerous differences between the LV and VR-2332 viruses occurred throughout the 3' genomic sequences that coded for ORFs 2 through 7, as well as the 3' untranslated region. These differences were due to nucleotide substitutions, base deletions and base additions. The sequence divergence arose, presumably, from error-prone replication, and suggests that the viral replicase has poor fidelity and lacks proofreading activity.

EXAMPLE 6

Amino Acid Residue Sequence Comparison and Immunological Cross-Rractivity

An initial survey indicated that the deduced proteins from these six VR-2332 ORFs roughly corresponded to known ORFs 2 through 7 in each of LV virus, LDV, and EAV. Accordingly, a detailed comparative study was performed to determine differences between the amino acid residue sequences of the VR-2332 and the LV virus, as well as the other Arteriviridae including LDV and EAV. The amino acid sequence comparison was performed using GCG (University of Wisconsin, Madison, Wis.) and Intelligenetics, Inc. (Mountain View, Calif.) software. Sequence ID No. 1 includes the VR-2332 sequence for the 3'-most 3442 bases of the VR-2332 nucleotide sequence, as well as the 5'-most 84 bases preceding the start of ORF 2. These 3358 nucleotides encode the structural proteins of the virus, and include six ORFs with each ORF corresponding to Sequence ID Nos. 2–13. These VR-2332 ORFs have varying degrees of homologies in comparison with LV ORFs 2–7 as well as other members of the Arteriviridae family including LV virus, LDV, and EAV. More specifically, a comparative sequence analysis indicates a degree of amino acid sequence homology between the VR-2332 virus and the LV virus ranging from 55% in ORF 5 to 79% in ORF 6. Table 1 provides the results of this Arteriviridae family comparison.

TABLE 1

Percent Amino Acid Identity of VR-2332 with LV, LDV and EAV*

| ORF | LV | LDV | EAV |
|-----|----|----|-----|
| 2 | 63 | 43 | 23 |
| 3 | 60 | 41 | 39 |
|   |    | (31) | (25) |
| 4 | 70 | 39 | 22 |
| 5 | 55 | 52 | 28 |
| 6 | 79 | 52 | 27 |
| 7 | 64 | 56 | 26 |

*Homologies were determined using the Needleman-Wunsch algorithm to align sequences and dividing the number of identical amino acids by the total number of amino acids in the smaller ORF. Since ORF 3 of LDV and EAV is significantly smaller than VR-2332 ORF 3, the homology based on division by VR-2332 is also shown in parentheses.

While the VR-2332 ORFs were most like those of LV virus, the comparison of VR-2332 to LDV indicated that VR-2332 has shared an evolutionary history with LDV. VR-2332 shared 55% identity with ORF 5 of LV virus, but had the lowest overall degree of homology with LV. The VR-2332 ORF 5 had the greatest degree of overall homology with respect to its LDV counterpart. VR-2332 ORF 5, which had about 52% identity with LDV ORF 5, was only slightly more similar to LV than it was to LDV. When VR-2332 was compared to LDV, the homologies were higher in ORFs 5, 6, and 7 than in ORFs 2, 3, and 4. Other than providing a basis for explaining the observed antigenic variance between these related viruses, the further significance of these divergences is unclear, in part because the functions of proteins derived from ORFs 2, 3, and 4 are unknown.

These amino acid sequence analyses also demonstrated that, with few exceptions, the sequence differences were widely distributed. The principal differences were located in the signal-sequence coding 5' ends of the ORFS, and ORF 4 in the region of amino acid residues 50–70.

Both VR-2332 and the LV virus have been identified as different infectious agents that cause the PRRS clinical signs, but have demonstrated very little, if any, immunological cross-reactivity, as reported by Wensvoort et al. (see above). Nevertheless, the deduced amino acid sequence from the 3' end of VR-2332 (Sequence ID Nos. 3, 5, 7, 9, 11, and 13) revealed a genomic organization that is characteristic of the Arteriviridae, i.e., overlapping coding regions in different reading frames of Sequence ID No. 1.

A dot-matrix analysis was performed by utilizing the GCG software to compare the predicted protein structures for ORFs 2–7 of VR-2332 and the LV virus. As will be understood by those skilled in the art, the dot matrix analysis was performed according to a conventional technique by utilizing a sliding window of 21 amino acids with a requirement of 13 identical residues at each location. This analysis demonstrated that all of the ORFs were substantially collinear between VR-2332 and LV, i.e., the respective viral structures were very similar despite extensive amino acid diversity. The nearly collinear nature of the VR-2332 and LV ORFs also indicated that the amino acid residue differences did not arise from genomic rearrangements. Table 2 provides a detailed comparison of the various deduced amino acid residues that correspond to the respective ORFs in VR-2332 and LV virus.

TABLE 2

Comparison of VR-2332 and LV Virus ORFs 2–7

| ORF | Amino Acids | | Predicted KD | | pI | | Glycosylation Sites | |
|---|---|---|---|---|---|---|---|---|
| | 2332 | LV | 2332 | LV | 2332 | LV | 2332 | LV |
| 2 | 256 | 249 | 29.4 | 28.4 | 11.0 | 10.2 | 2 | 2 |
| 3 | 254 | 265 | 29.0 | 30.6 | 8.1 | 9.4 | 7* | 7 |
| 4 | 178 | 183 | 19.5 | 20.0 | 7.9 | 6.1 | 4 | 4 |
| 5 | 200 | 201 | 22.4 | 22.4 | 8.3 | 8.2 | 3 | 2 |
| 6 | 174 | 173 | 19.0 | 18.9 | 11.3 | 11.9 | 1 | 2 |
| 7 | 123 | 128 | 13.5 | 13.8 | 10.4 | 11.2 | 1* | 1 |

*Not all predicted sites are identical.

While these studies demonstrated that VR-2332 was more closely related to the LV virus than were other members of the Arteriviridae, the homologies were much lower than expected for two viruses that cause the same disease; i.e., substitutions, deletions and additions occurred throughout the comparative sequences. The predicted proteins had different molecular weights, different isoelectric points, and different predicted glycosylation sites (Table 2).

Although the amino acid homologies were substantially less than expected for viruses that appear to cause an identical disease, the findings were consistent with the striking antigenic diversity reported from serological studies by Wensvoort et al. These studies provided an explanation as to why there is observed little, if any, serological cross-reactivity between naturally occurring VR-2332 and LV antigens. Antigenic differences between VR-2332 and LV virus are due to immunological responses of swine to the dissimilar amino acid sequence regions of the viruses.

EXAMPLE 7

Hydropathy Profile Studies

Other characteristics of the predicted proteins including the hydropathy profiles and percent basic character were compared. The results confirmed that the two viruses (LV and VR-2332) had functions and structures that were significantly more similar than was indicated by the amino acid comparison of Example 6 and immunological cross-reactivity reports.

Comparative hydropathy profiles were created utilizing the EUGENE software package from Daniben Systems Inc. of Cincinnati, Ohio, based upon the deduced amino acid residue sequences for VR-2332 (Sequence ID Nos. 2–13) and LV virus (Sequence ID Nos. 14–26). These profiles indicated that the ORFs of VR-2332 and LV virus correspond structurally despite significant amino acid residue sequence differences. These results are consistent with the observed biological similarities, which contrast with the distinct serological properties between the VR-2332 and LV virus isolates.

The hydropathy profiles compared each corresponding ORF in VR-2332 and the LV virus to indicate that protein structures and protein functions were conserved despite the extensive sequence differences. These profiles demonstrated highly similar regions of uncharged and charged amino acids, and are accurate predictors of similar functionality in membrane associated proteins of regions that either span or do not span the membrane. Thus, the VR-2332 proteins are similar in structure and function to those of LV virus, but extensive amino acid differences in the viral proteins account for the extensive differences in serological cross-reactivity.

FIGS. 3, 3A, 3B, and 3C depict the amino acid sequence alignment and hydropathy profiles for ORF 7 of VR-2332 (Sequence ID No. 13) and LV (Sequence ID No. 26). This ORF is located at the 3' end of the LV genome where the nucleocapsid protein has also been mapped in LDV and EAV, as reported by Godeny et al., *Map location of lactate dehydrogenase-elevating virus (LDV) capsid protein (Vp1) gene*, 177 Virol. 768–771 (1990), and de Vries et al., *Structural proteins of equine arteritis virus*, 66 J. Virol. 6294–6303 (1992). ORF 7 most likely forms the nucleocapsid protein in the PRRS virus. The protein was 64% similar between VR-2332 and LV virus, and VR-2332 ORF 7 was smaller by five amino acids. Nevertheless, the N-terminal half of both proteins encoded by ORF 7 was 26–28% basic and the hydrophobicity profiles were nearly identical. The basic residues presumably facilitate interactions with the RNA genome.

FIGS. 4, 4A, 4B, and 4C depict the amino acid sequence alignment and hydropathy profiles for ORF 6 of VR-2332 (Sequence ID No. 11) and LV (Sequence ID No. 24). ORF 6 was the VR-2332 protein that was most similar to its LV virus counterpart, and was the only ORF that coded for an apparent amino terminal signal sequence. The LV and VR-2332 proteins shared 79% identity and one predicted glycosylation site (the LV virus had an additional site not found in VR-2332). Hydropathy profiles of ORF 6 of VR-2332, LV and EAV all showed three highly hydrophobic regions in the N-terminal half of the protein that indicate membrane spanning domains. These regions appear to be a conserved characteristic of all members of the Arteriviridae.

FIGS. 5, 5A, 5B, and 5C depict the amino acid sequence alignment and hydropathy profiles for ORF 5 of VR-2332 (Sequence ID No. 9) and LV (Sequence ID No. 22). ORF 5 appears to encode an envelope protein in the Arteriviridae because of its hydropathy profile and putative glycosylation sites. Similarly, according to de Vries et al. (see above) the $G_L$ or ORF 5 protein for EAV is glycosylated, VR-2332 ORF 5 contains three potential glycosylation sites, two of which are shared with LV. The LV and VR-2332 hydropathy profiles are highly similar although their percent identity (55%) was the lowest of all ORFs. In particular, only seven residues in the amino terminal 40 amino acids are the same, yet the hydropathy profiles are virtually identical. Potential membrane spanning domains between residues 65 and 130 are more pronounced in VR-2332.

FIGS. 6, 6A, 6B, and 6C depict the amino acid sequence alignment and hydropathy profiles for ORF 4 of VR-2332 (Sequence ID No. 7) and LV (Sequence ID No. 20). After ORF 6, ORF 4 is the most highly conserved ORF. The carboxyl terminus also is exceptionally hydrophobic in both viruses. Five putative membrane spanning domains are much more distinct in VR-2332 than in LV virus.

FIGS. 7, 7A, 7B, and 7C depict the amino acid sequence alignment and hydropathy profiles for ORF 3 of VR-2332 (sequence ID No. 7) and LV (sequence ID No. 18). ORF 3 is 60% similar between VR-2332 and LV virus. Nevertheless, ORF 3 is the least similar protein between the two viruses based on hydropathy profiles and by carboxyl terminal deletions of 12 amino acids in VR-2332. As a result of these differences, the corresponding LV protein has a strongly hydrophilic region centered on residue 240, whereas the VR-2332 protein appears amphipathic in this region. The nominal molecular mass of ORF 3 is approximately 30 kD, but it contains seven potential glycosylation sites in each virus, so that its apparent size can be significantly greater.

FIGS. 8, 8A, 8B, and 8C depict the amino acid sequence alignment and hydropathy profiles for ORF 2 of VR-2332 (Sequence ID No. 5) and LV (Sequence ID No. 16). ORF 2 was determined to be the largest of the 3' ORFs in VR-2332, and coded for the expression of 256 amino acids. It had a highly basic isoelectric point of 11.0, which was exceeded only by ORF 6, which had a pI of 11.3. The differences in amino acid sequence between VR-2332 and LV virus were distributed throughout the ORF, but the principal effect on the hydropathy profile appeared in the amino terminus.

FIG. 9 VR-2332 depicts an alignment of the 3' untranslated sequence following ORF 7 in VR-2332 and LV virus. This region consisted of 151 nucleotides and a poly A tail of 19 to 20 bases in VR-2332. Similarly, the LV virus had a noncoding region of 115 bases. Bases 50–171 of the VR-2332 non-coding region of shared a strong homology to bases 13–135 of the LV non-coding region.

EXAMPLE 8

Isolation of VR-2332 RNA

Viral RNA from infected cell supernatants is isolated for use in reverse transcription and PCR amplification reactions that selectively amplify either the VR2332 or the LV viral nucleotides as a diagnostic tool for LV or PRRS. Additionally, PCR amplification is used to produce quantities of nucleotides for use in vaccines.

As a diagnostic measure, swine lung tissue homogenates are preferably obtained by selecting tissue samples from alveolar abnormalities that are typical of PRRS; homogenizing these samples; mixing the homogenate with an appropriate physiological saline, e.g., Minimum Essential Medium, to a 10% (w/v) tissue concentration; and filtering the homogenate mixture through a series of filters having 0.45, 0.2 and 0.1 micron openings.

The filtered homogenate is used as inoculum to infect cells of an appropriate cell line, e.g., monkey kidney cells or MA-104. The inoculated culture is incubated until a culture stock is obtained having a high virus titer from about log 5 to log 7.

A first solution is prepared to include 5M guanidinium isothiocyanate, 50 mM Tris HCl pH 7.5, 25 mM EDTA, 0.5 w/v Sarcosyl, and 1% (v/v)2-mercaptoethanol. A 10 ml aliquot of this solution is mixed with 100 microliters of 2-mercaptoethanol. A 2 ml portion of the virus stock culture is mixed in a tube with 2 ml of the first solution aliquot, as is 0.4 ml of 2M sodium acetate, 4 ml phenol, and 1 ml of a chloroform-isoamyl alcohol solution mixed at a ratio of 24 parts of chloroform to 1 part of isoamyl alcohol. The virus-containing mixture is vortexed briefly after the addition of each reagent. The final mixture is vortexed for thirty seconds, chilled on ice for 15 seconds, then centrifuged at 8000 rpm for 20 minutes at 4° C. in a JA-20 rotor. The aqueous phase will separate to the top upon centrifugation, and contains the RNA of interest.

The aqueous phase is decanted and transferred to a new tube. About 4 ml of sterile water containing 2% by volume of diethylpyrocarbonate before autoclaving, is added to this second tube, as is 4 ml phenol, and 1.6 ml of the 24:1 chloroform-isoamyl alcohol mixture. These ingredients are vortexed, chilled on ice for 15 minutes, centrifuged at 8000 rpm for 20 minutes at 4° C. in a JA-20 rotor, and the aqueous phase is again extracted. The resultant aqueous extract is mixed with an equal volume of isopropanol, and chilled on ice for 1 hour to precipitate the RNA.

The precipitated RNA is sedimented by centrifugation at 8000 rpm for 20 minutes at 4° C. in a JA-20 rotor. The isopropanol is decanted, and the invisible RNA pellet is dissolved in 0.3 ml of a solution containing 5M guanidinium isothiocyanate, 50 mM Tris HCl pH 7.5, 25 mM EDTA, 0.5% Sarcosyl, and 1% 2-mercaptanol, and 0.1% 2-mercaptoethanol. The solution containing the dissolved pellet is transferred to a 1.5 ml microfuge tube, and the RNA is again precipitated with 0.3 ml of isopropanol for 1 hour on ice. The chilled solution is centrifuged at 15,000 rpm in a microfuge for 10 minutes, after which the isopropanol is decanted. The resultant pellet is washed with about 0.5 ml of a solution containing 75% ethanol mixed with 25% water containing 0.2% diethyl pyrocarbonate by volume. After washing, the mixture is vortexed, and centrifuged for 5–10 minutes. The alcohol is decanted, and the RNA pellet is vacuum-dried for about 3 minutes. The pellet is dissolved in 50 ml of water containing 0.2% diethylpyrocarbonate by volume.

EXAMPLE 9

Reverse Transcription of OF RNA to form cDNA

The solution from Example 8 containing RNA and the 0.2% diethylpyrocarbonate water is next subjected to reverse transcription of the RNA to produce complimentary fragments of cDNA. This procedure is preferably conducted by using commercially available kits, such as the RT-PCR kit from Perkin-Elmer. The kits are used according to the manufacturers instructions, which describe the proper use of kit reagents.

By way of example, a master mixture is prepared from named reagents of the RT-PCR kit by mixing 4 $\mu$l MgCl$_2$, 2 $\mu$l of 10X buffer, 2 $\mu$l dGTP, 2 $\mu$l DATP, 2 $\mu$l dCTP, 2 $\mu$l TTP, 1 $\mu$l RNase inhibitor, and 1 $\mu$l of reverse transcriptase. A 3 $\mu$l aliquot of the RNA and 0.2% diethylpyrocarbonate water mixture is placed into a microfuge tube taking care, if necessary, to dilute the aliquot with 0.2% diethylpyrocarbonate water so as to include no more than 1 ug of total RNA in the tube. The kit contains a mixture of random hexamers, and 1 $\mu$l of this mixture is added to the RNA and diethylpyrocarbonate water. The solution then is optionally heated to a temperature from about 65–70° C. for 5 to 10 minutes, and placed on ice. The 16 $\mu$l of master mix is added to the sample, and incubated at room temperature for about 10 minutes. Thereafter, the tube is incubated in a thermal cycler under the following conditions: 42° C. for 15 minutes, 99° C. for 5 minutes, and 5° C. for 5 minutes. The tube is removed from the thermal cycler and stored at 4° C. The result of this reverse transcriptase reaction contains cDNA, which is subsequently subjected to PCR amplification.

EXAMPLE 10

Selective PCR Amplification of cDNA

In preparation for PCR amplification, a master mixture of the following reagents is prepared. 1 μl of Mgcl$_2$, 2 μl of 10× buffer, 0.5 μl of 5' primer, 0.5 μl of 3' primer, 15.875 μl of sterile water, and 0.125 μl of Taq polymerase. The 5' and 3' primers should have a concentration of approximately 10 uM, and are preferably comprised of synthetic nucleotides based upon the sequences listed below in Table 3. A 5 μl aliquot of the reverse transcriptase reaction solution from Example 9 is added to 20 μl of master mixture. The resultant 25 μl combination of master mixture and reverse transcriptase cDNA aliquot is overlain in a tube with 100 μl of mineral oil. The tube is incubated in a thermal cycler under the following conditions: 93° C. for 4 minutes for one cycle; 55° C. for 30 seconds, 72° C. for 45 seconds, and 93° C. for 45 seconds, for 30 cycles; and 55° C. for 30 seconds, followed by 72° C. for 10 minutes for one cycle. After these 32 cycles, the solution is then maintained at 4° C. until it is removed from the thermal cycler. The resultant solution, which contains PCR-amplified cDNA, is analyzed on an agarose gel.

The preferred agarose gel includes 1.5% agarose mixed with TAE buffer, i.e., 1.5 grams of agarose per 100 ml of buffer. The mixture is melted in a microwave, and 1 μl of 10 mg/ml ethidium bromide solution is added per 100 ml of the gel. The mixture is poured into a casting stand, and allowed to harden for 30–45 minutes. A 5 μl aliquot of the PCR reaction solution is added into a tube, and 2 μl of a UV-sensitive running dye is added to the aliquot. An additional aliquot of 1–2 μl of an appropriate molecular weight marker is also added, such as a 100 base ladder from Gibco-BRL. The gel is placed in an electrophoresis chamber and the chamber is filled with a conventional TAE running buffer. Samples are loaded, and run at 80 volts for 1 hour. The electrophoresed PCR products are visualized under UV light. The PCR generated fragments that are visualized under UV light after the agarose gel electrophoresis are subjected to DNA sequencing for unambiguous confirmation of the identity of the viral nucleotide product.

EXAMPLE 11

Oligonucleotide Design for Selective PCR Amplification or Hybridization

The 5' and 3' primers that are used in the PCR amplification of Example 10 are preferably constructed, according to conventional protocols or on commercial order, as synthetic nucleotide sequences that replicate regions of interest in the VR-2332 genome. The primer design preferably includes selecting appropriate primers as the entire amino acid-coding sequences of the viral protein, selected ORFs, or, most preferably, coding regions for amino acid sequences representing protein fragments.

The preferred oligonucleotides are selected to include those which specifically target small portions of the VR-2332 coding region, but are incapable of annealing with LV-derived nucleotides. These preferred oligonucleotides are used as primers for PCR amplification techniques to replicate long sequences of cDNA that are selected by the primers for use in vaccines and methods of vaccination. Similarly, the oligonucleotides are also used as probes for subsequent hybridization, cloning, and host expression of protein fragments and nucleotide products for subsequent use in vaccines.

Preferred examples of the cDNA coding regions for expressed protein fragments that are selected for use in producing vaccines include those in which the translated amino acid terminal hydrophobic sequences are removed, as these terminal sequences are usually not present on mature forms of the viral protein. Selected cDNA coding regions can also code for protein fragments in which putative membrane-spanning sequences are removed, as the membrane-spanning sequences likely will not induce immune responses, and this removal generally simplifies the production of immunologically-sensitive proteins by recombinant DNA techniques.

The sequences listed in Table 3 below represent exemplary primers with positional reference to the accompanying Sequence Listing. All sequences are provided in a 5' to 3' orientation. By way of example, Primer A represents the sequence 5'-GCTGTTAAACAGGGAGTGG-3' (Sequence ID No. 31). Primer A' is the inverse compliment of the sequence 5'-GTCACCTATTCAATTAGGG-3' (Sequence ID No. 32 which is Sequence ID No. 1 positions 3271–3289), i.e., the sequence 5'-CCCTAATTGAATAGGTGAC-3' (Sequenece ID No. 33) in which reverse-ordered complimentary nucleotides have been substituted for the sequence at positions 3271–3289.

TABLE 3

| | | Positional Reference | | |
|---|---|---|---|---|
| Primer | Description | Seq. ID | From | To |
| A | VR-2332 ORF 7 based primer | 1 | 2783 | 2801 |
| A' | VR-2332 ORF 7 based inverse compliment of the VR-2332 sequence | 1 | 3271 | 3289 |
| B | VR-2332 ORF 6 based primer | 1 | 2289 | 2307 |
| B' | VR-2332 ORF 6 based inverse compliment of the VR-2332 sequence | 1 | 2862 | 2880 |
| C | LV ORF 6 based primer | 14 | 14112 | 14131 |
| C' | LV ORF 6 based inverse compliment of the LV sequence | 14 | 14551 | 14570 |
| D | LV ORF 7 based primer | 14 | 14575 | 14594 |
| D' | LV ORF 7 based inverse compliment of the LV sequence | 14 | 14955 | 14974 |
| E | VR-2332 ORF 7 based primer * | 1 | 2814 | 2832 |
| E' | VR-2332 ORF 7 based inverse compliment of the VR-2332 sequence ** | 1 | 3273 | 3291 |
| F | VR-2332 ORF 7 based primer *** | 1 | 2816 | 2834 |
| F' | VR-2332 ORF 7 based inverse compliment of the VR-2332 sequence **** | 1 | 3181 | 3198 |

* A synthetic oligonucleotide may be constructed to include a BamHI restriction site with this sequence, i.e., the additional 5'-GCGGATCC nucleotides, for insertion into Pharmingen's pAcGP67B plasmid vector.
** A synthetic oligonucleotide may be constructed to include an inverse complimentary EcoRI restriction site with this sequence, i.e., the additional 5'-CCGAATTC nucleotides, for insertion into Pharmingen's pAcGP67B plasmid vector.
*** A synthetic oligonucleotide may be constructed to include a Ndel restriction site with this sequence, i.e., the additional 5'-GCGCA nucleotides, for insertion into Novagen's pET25b plasmid vector.
**** A synthetic oligonucleotide may be constructed to include an inverse complimentary HindIII restriction site with this sequence, i.e., the additional 5'-GCGAAGCT nucleotides, for insertion into Novagen's pET25b plasmid vector.

Primers A and A' of Table 3 will selectively amplify the VR-2332 ORF 7 protein-coding nucleotides in a manner that distinguishes the VR-2332 nucleotides from other viral nucleotide isolates, including LV isolates. Similarly, Primers B and B' will selectively amplify the VR-2332 ORF 6 protein-coding nucleotides in a manner that distinguishes the VR-2332 nucleotides from other viral nucleotide isolates. On the other hand, Primers C and C', will selectively amplify the ORF 6 coding region of LV virus without amplifying VR-2332 ORF 6. Primers D and D' will selectively amplify LV ORF 7 without amplification of VR-2332 ORF 7.

The preferred oligonucleotides of Table 3 are used for diagnosis of the specific PRRS-causative strain or virus through attempted PCR amplification of cDNA or conventional hybridization reactions. By way of example, if the PRRS signs are confirmed clinically in a diseased animal and if the primers that are specific for amplification of the Lelystad virus (e.g., Primers C, C' and D, D') fail to produce cDNA amplification in the PCR reaction, then the absence of LV cDNA would be consistent with a diagnosis of VR-2332 infection. On the other hand, the failure of VR-2332 primers A, A' or B, B' in PCR amplification would be consistent with a diagnosis of LV infection.

In cases where the presence of viral cDNA is confirmed by hybridization to these primer or probe sequences of Table 3, the hybridization occurs in solution with either cDNA or RNA affixed to a solid support such as nitrocellulose or nylon membranes. The recovered hybridized product is detected by conventional radioactive or non-radioactive techniques, which indicate the presence of viral nucleic acid sequence. Those skilled in the art will understand that an elementary list of diagnostic techniques includes dot-blot hybridization, slot-blot hybridization, solution hybridization, southern blot, northern blot, and RNase protection assays.

EXAMPLE 12

Cloning of VR-2332 Protein Coding Sequences in Host Expression Systems for the Production of Recombinantly Derived Viral Proteins Selected portions of the VR-2332 nucleotide sequence (Sequence ID Nos. 1, 2, 4, 6, 8, 10, and 12) are used to clone an open reading frame, or a plurality of open reading frames, into a commercially available plasmid, that is designed for protein expression in a host organism. Examples of commercially available or self-designated systems that are used for the expression of viral proteins in eukaryotic or prokaryotic cells follow.

The commercially available eukaryotic baculovirus system from Pharmingen of San Diego, California, which includes the vector pAcGP67B is preferred for use with Primers C and C'. As indicated in Table 3, Primers C and C' may be provided with respective BamHI and EcoRI restriction sites formed of synthetically joined nucleotides for use in linking these primers with the pAcGP67B vector. By this method, the resultant amplified cDNA would incorporate substantially the entire coding region of VR-2332 ORF 7, and would also have a 5'-most BamHI site as well as a 3'-most EcoRI site. These restriction sites are used to place the VR-2332 coding region under the control of the appropriate pAcGP67B promoter and termination sequences for eukaryotic host expression of VR-2332 ORF 7 proteins.

Prokaryotic host expression of viral proteins is accomplished in a variety of commercially available host expression systems. The PET system from NovaGen of Madison, Wisconsin is preferred for prokaryotic expression, and includes the vector pET25b. The PET system is preferred for use with Primers D and D', which may be provided with respective NdeI and HindIII restriction sites for use in placing the VR-2332 ORF 7 coding region under the control of appropriate promoter and termination sequences.

The protein corresponding to VR-2332 ORF 7 of Sequence ID Nos. 12 and 13 is expressed by amplifying selected protein coding sequences corresponding to the putative mature protein of ORF 7. This amplification procedure will follow the RT-PCR amplification procedure that is outlined in Examples 8, 9, and 10. The PCR primers are preferably designed to include NdeI and HindIII restriction sites for cloning into the pET25b vector. These sites will result in a protein without a pelB leader or HisTag sequence, which provide alternative options for other expression systems. The mature protein is expressed without a signal peptide sequence by beginning the nucleotide sequence to code for either amino acid number 20 or number 30. The PCR fragments are cloned into the pET25b vector-amplified sequence and used in a host expression system.

In selecting protein coding regions other than ORF 7, it is advantageous to delete or truncate certain protein coding regions, e.g., deletion of the membrane-spanning C-terminal 17 amino acids from ORF 4 will likely direct antibody responses to biologically relevant portions of the protein.

The recombinant clones are transformed into BL21 cells for induction by isopropyl-$\beta$-D-thiogalactopyranoside ("IPTG"). After induction and an appropriate incubation, the expressed recombinant bioprotein is detected on a gel by comparing lysates from induced and uninduced cells. Inclusion body preps are washed with urea or guanidine at a concentration that removes contaminating proteins without solubilizing the ORF 4 protein. Aggregates are resolublized in urea and refolded in oxidized and reduced glutathione. The resultant soluble, dialyzed protein is further purified by ion-exchange and size exclusion chromatography.

EXAMPLE 13

Induction of an Immune Response in an Animal by Injection of Recombinant Viral Proteins The purified proteins from bacterial or eukaryotic expression systems, as produced in Example 12, are injected into animals by conventional immunization routes to elicit immune responses sufficient to immunize the animal against the VR-2332 strains of PRRS virus. The proteins alone, or in combination with a conventional adjuvant, are administered by intramuscular injection, intradermal injection, subcutaneous injection, or otherwise.

As an alternative, live molecularly engineered bacteria or virus that express proteins corresponding to VR-2332 sequences are administered to animals by injection of the expression of VR-2332 proteins in vivo. This in vivo expression of recombinant proteins will also elicit an immune response to the VR-2332 virus.

EXAMPLE 14

The use of VR-2332 DNA to Induce a Direct Immune Response in an Animal

VR-2332 based oligonucleotide fragments, which code for ORFs or fragmentary portions of ORFs, are used to generate a direct immune response in an animal. This method generally follows the procedure described in Omer et al., 259 Science 1745–1749 (1993). The DNA is preferably included in plasmid constructs that are grown in bacteria, purified, and injected into animals by intramuscular injection, intradermal injection, or by other routes. The injected animal will typically express the cloned protein, and produce a corresponding immune response to the protein that is expressed.

REFERENCES

The following references pertain to PRRS viruses, and are hereby incorporated by reference herein.

Benfield, D. A., Nelson, E., Collins, J. E., Harris, L., Goyal, S. M., Robison, D., Christianson, W. T., Morrison, R. B., Gorcyca, D. E., and Chladek, D. W. (1992). Characterization of swine infertility and respiratory syndrome (SIRS) virus (isolate ATCC VR-2332). J. Vet. Diagn. Invest. 4, 127–133.

Chomczynski, P. and Sacchi, N. (1987). Single-step method of RNA isolation by acid guanidinium thiocyanate-phenol-chloroform extraction. Anal. Biochem. 162, 156–159.

Collins, J. E., Benfield, D. A., Christianson, W. T., Harris, L., Hennings, J. C., Shaw, D. P., Goyal, S. M., McCullough, S., Morrison, R. B., Joo, H. S., Gorcyca, D. E., and Chladek, D. W. (1992). Isolation of swine infertility and respiratory syndrome virus (isolate ATCC VR-2332) in North America and experimental reproduction of the disease in gnotobiotic pigs. J. Vet. Diagn. Invest. 4, 117–126.

Conzelmann, K., Visser, N., Van Woensel, P. and Thiel, H. (1993). Molecular characterization of porcine reproductive and respiratory syndrome virus, a member of the arteriderus group. Virology 193, 329–339.

den Boon, J. A., Snijder, E. J., Chirnside, E. D., de Vries, A. A. F., Horzinek, M. C., and Spann, W. J. M. (1991). Equine arteritis virus is not a togavirus but belongs to the coronavirus superfamily. J. Virol. 65, 2910–2920.

de Vries, A. A. F., Chirnside, E. D., Horzinek, M. C., and Rottier, P. J. M. (1992). Structural proteins of equine arteritis virus. J. Virol. 66, 6294–6303.

Godeny, E. K., Speicher, D. W., and Brinton, M. A. (1990). Map location of lactate dehydrogenase-elevating virus (LDV) capsid protein (Vp1) gene. Virol. 177, 768–771.

Godeny, E. K., Zeng, L., Smith, S. L., and Brinton, M. A. (1993). In Proceedings of the 9th International Congress of Virology, p 22, August 8–13, Glasgow, Scotland.

Gravell, M., W. T. London, M. E. Leon, A. E. Palmer and R. S. Hamilton. Proc. Soc. Exp. Biol. Med. 181, 112–119.

Hill, H. (1990). Overview and History of Mystery Swine Disease (Swine Infertility and Respiratory syndrome). In: Proceedings of the Mystery Swine Disease Committee Meeting, Oct. 6, Denver Colo., pp. 29–30. Livestock Conservation Institute, Madison, Wis.

Kuo, L., Harty, J. T., Erickson, L., Palmer, G. A., and Plagemann, P. G. W. (1991). A nested set of eight mRNAs is formed in macrophages infected with lactate dehydrogenase-elevating virus. J. Virol. 65, 5118–5123.

Meulenberg, J. J. M., Hulst, M. M., de Veijer, E. J., Moonen, P. L. J. M., den Besten, A., de Kluyver, E. P., Wensvoort, G., and Moormann, R. J. M. (1993). Lelystad virus, the causative agent of porcine epidemic abortion and respiratory syndrome (PEARS), is related to LDV and EAV. Virology 192, 62–72.

Paton, D. J., Brown, I. H., Edwards., S. and Wensvoort, G. (1991). Blue ear disease of pigs. Vet Rec. 128, 617.

Plagemann, P. G. W. and Moennig, V. (1992). Lactate dehydrogenase-elevating virus, equine arteritis virus and simian hemorrhagic fever virus: a new group of positive-strand RNA viruses. Adv. Vir. Res. 41, 99–192.

Pol, J. M. A., Van Dijk, J. E., Wensvoort, G., and Terpstra, C. (1991). Pathological, ultrastructural, and immunohistochemical changes caused by Lelystad virus in experimentally induced infections of mystery swine disease (synonym: porcine epidemic abortion and respiratory syndrome (PEARS)). Vet. Q. 13, 137–143.

Spaan, W. J. M., Cavanagh, D. and Horzinek, M. C. (1988). Coronaviruses: structure and genome erxpression. J. Gen. Virol. 69, 2939–2952.

Wensvoort, G., Terpstra, C., Pol, J. M. A., Ter Laak, E. A., Bloemraad, M., De Kluyver, E. P., Kragten, C., Van Buiten, L., Den Besten, A., Wagenaar, F., Broekhuijsen, J. M., Moonen, P. L. J. M., Zetstra,T., De Boer, E. A., Tibben, H. J., De Jong, M. F., Van't Veld, P., Groenland, G. J. R., Van Gennep, J. A., Voets, M. T., Verheijeden, J. H. M., and Braamskamp, J. (1991). Mystery swine disease in the Netherlands: the isolation of Lelystad virus. Vet. Q. 13, 121–130.

Wensvoort, G., de Kluyver, E. P., Pol, J. M. A., Wagenaar, F., Moormann, R. J. M., Hulst, M. M. Bloemraad, R., den Besten, A., Zetstra, T. and Terpstra, C. (1992a). Lelystad virus, the cause of porcine epidemic abortion and respiratory syndrome: a review of mystery swine disease research at Lelystad. Vet. Micro. 33, 185–193.

Wensvoort, G., de Kluyver, E. P., Lujtze, E. A., den Besten, A., Harris, L., Collins, J. E., Christianson, W. T. and Chladek, D. (1992b). Antigenic comparison of Lelystad virus and swine infertility and respiratory syndrome (SIRS) virus. J. Vet. Diagn. Invest. 4, 134–138.

---

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 3358 base pairs
      (B) TYPE: nucleic acid (C) STRANDEDNESS: double
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Arteriviridae (Unclassified)
        (B) STRAIN: VR-2332

(ix) FEATURE:
        (A) NAME/KEY: misc_feature
        (B) LOCATION: 1..768
        (C) IDENTIFICATION METHOD: experimental
        (D) OTHER INFORMATION: /evidence= EXPERIMENTAL
            /standard_name= "VR-2332 ORF2"

(ix) FEATURE:
        (A) NAME/KEY: misc_feature
        (B) LOCATION: 624..1385
        (D) OTHER INFORMATION: /standard_name= "VR-2332 ORF 3"

(ix) FEATURE:
        (A) NAME/KEY: misc_feature
        (B) LOCATION: 1169..1701
        (D) OTHER INFORMATION: /standard_name= "VR-2332 ORF 4"

(ix) FEATURE:
        (A) NAME/KEY: misc_feature
        (B) LOCATION: 1716..2315
        (D) OTHER INFORMATION: /standard_name= "VR-2332 ORF 5"

(ix) FEATURE:
        (A) NAME/KEY: misc_feature
        (B) LOCATION: 2303..2824
        (D) OTHER INFORMATION: /standard_name= "VR-2332 ORF 6"

(ix) FEATURE:
        (A) NAME/KEY: misc_feature
        (B) LOCATION: 2817..3185
        (D) OTHER INFORMATION: /standard_name= "VR-2332 ORF 7"

(xi) SEQUENCE DESCRIPTION: SEQ ID NO:1:

```
ATGAAATGGG GTCCATGCAA AGCCTTTTTG ACAAAATTGG CCAACTTTTT GTGGATGCTT      60

TCACGGAGTT CTTGGTGTCC ATTGTTGATA TCATTATATT TTTGGCCATT TTGTTTGGCT     120

TCACCATCGC CGGTTGGCTG GTGGTCTTTT GCATCAGATT GGTTTGCTCC GCGATACTCC     180

GTACGCGCCC TGCCATTCAC TCTGAGCAAT TACAGAAGAT CTTATGAGGC CTTTCTTTCC     240

CAGTGCCAAG TGGACATTCC CACCTGGGGA ACTAAACATC CTTGGGGAT GCTTTGGCAC      300

CATAAGGTGT CAACCCTGAT TGATGAAATG GTGTCGCGTC GAATGTACCG CATCATGGAA     360

AAAGCAGGGC AGGCTGCCTG GAAACAGGTG GTGAGCGAGG CTACGCTGTC TCGCATTAGT     420

AGTTTGGATG TGGTGGCTCA TTTTCAGCAT CTAGCCGCCA TTGAAGCCGA GACCTGTAAA     480

TATTTGGCCT CCCGGCTGCC CATGCTACAC AACCTGCGCA TGACAGGGTC AAATGTAACC     540

ATAGTGTATA ATAGCACTTT GAATCAGGTG TTTGCTATTT TTCCAACCCC TGGTTCCCGG     600

CCAAAGCTTC ATGATTTTCA GCAATGGTTA ATAGCTGTAC ATTCCTCCAT ATTTTCCTCT     660

GTTGCAGCTT CTTGTACTCT TTTTGTTGTG CTGTGGTTGC GGGTTCCAAT ACTACGTACT     720

GTTTTTGGTT TCCGCTGGTT AGGGGCAATT TTTCTTTCGA ACTCACAGTG AATTACACGG     780

TGTGTCCACC TTGCCTCACC CGGCAAGCAG CCACAGAGAT CTACGAACCC GGTAGGTCTC     840

TTTGGTGCAG GATAGGGTAT GACCGATGTG GGGAGGACGA TCATGACGAG CTAGGGTTTA     900

TGATACCGCC TGGCCTCTCC AGCGAAGGCC ACTTGACTGG TGTTTACGCC TGGTTGGCGT     960

TCTTGTCCTT CAGCTACACG GCCCAGTTCC ATCCCGAGAT ATTCGGGATA GGGAATGTGA    1020
```

```
GTCGAGTTTA TGTTGACATC AAACATCAAC TCATCTGCGC CGAACATGAC GGGCAGAACA      1080

CCACCTTGCC TCGTCATGAC AACATTTCAG CCGTGTTTCA GACCTATTAC AACATCAAG       1140

TCGACGGCGG CAATTGGTTT CACCTAGAAT GGCTTCGTCC CTTCTTTTCC TCGTGGTTGG      1200

TTTTAAATGT CTCTTGGTTT CTCAGGCGTT CGCCTGCAAA CCATGTTTCA GTTCGAGTCT      1260

TGCAGATATT AAGACCAACA CCACCGCAGC GGCAAGCTTT GCTGTCCTCC AAGACATCAG      1320

TTGCCTTAGG CATCGCGACT CGGCCTCTGA GGCGATTCGC AAAATCCCTC AGTGCCGTAC      1380

GGCGATAGGG ACACCCGTGT ATGTTACCAT CACAGCCAAT GTGACAGATG AGAATTATTT      1440

ACATTCTTCT GATCTCCTCA TGCTTTCTTC TTGCCTTTTC TATGCTTCTG AGATGAGTGA      1500

AAAGGGATTT AAGGTGGTAT TTGGCAATGT GTCAGGCATC GTGGCTGTGT GTGTCAATTT      1560

TACCAGCTAC GTCCAACATG TCAAGGAGTT TACCCAACGC TCCCTGGTGG TCGACCATGT      1620

GCGGTTGCTC CATTTCATGA CACCTGAGAC CATGAGGTGG GCAACTGTTT TAGCCTGTCT      1680

TTTTGCCATT CTGTTGGCAA TTTGAATGTT TAAGTATGTT GGAGAAATGC TTGACCGCGG      1740

GCTGTTGCTC GCGATTGCTT TCTTTGTGGT GTATCGTGCC GTTCTGTTTT GCTGTGCTCG      1800

CCAACGCCAG CAACGACAGC AGCTCCCATC TACAGCTGAT TTACAACTTG ACGCTATGTG      1860

AGCTGAATGG CACAGATTGG CTAGCTAACA AATTTGATTG GGCAGTGGAG AGTTTTGTCA      1920

TCTTTCCCGT TTTGACTCAC ATTGTCTCCT ATGGTGCCCT CACTACCAGC CATTTCCTTG      1980

ACACAGTCGC TTTAGTCACT GTGTCTACCG CCGGGTTTGT TCACGGGCGG TATGTCCTAA      2040

GTAGCATCTA CGCGGTCTGT GCCCTGGCTG CGTTGACTTG CTTCGTCATT AGGTTTGCAA      2100

AGAATTGCAT GTCCTGGCGC TACGCGTGTA CCAGATATAC CAACTTTCTT CTGGACACTA      2160

AGGGCAGACT CTATCGTTGG CGGTCGCCTG TCATCATAGA GAAAAGGGGC AAAGTTGAGG      2220

TCGAAGGTCA TCTGATCGAC CTCAAAAGAG TTGTGCTTGA TGGTTCCGTG GCAACCCCTA      2280

TAACCAGAGT TTCAGCGGAA CAATGGGGTC GTCCTTAGAT GACTTCTGTC ATGATAGCAC      2340

GGCTCCACAA AAGGTGCTTT TGGCGTTTTC TATTACCTAC ACGCCAGTGA TGATATATGC      2400

CCTAAAGGTG AGTCGCGGCC GACTGCTAGG GCTTCTGCAC CTTTTGATCT TCCTGAATTG      2460

TGCTTTCACC TTCGGGTACA TGACTTTCGC GCACTTTCAG AGTACAAATA AGGTCGCGCT      2520

CACTATGGGA GCAGTAGTTG CACTCCTTTG GGGGGTGTAC TCAGCCATAG AAACCTGGAA      2580

ATTCATCACC TCCAGATGCC GTTTGTGCTT GCTAGGCCGC AAGTACATTC TGGCCCCTGC      2640

CCACCACGTT GAAAGTGCCG CACGGTTTCA TCCGATTGCG GCAAATGATA ACCACGCATT      2700

TGTCGTCCGG CGTCCCGGCT CCACTACGGT CAACGGCACA TTGGTGCCCG GGTTAAAAAG      2760

CCTCGTGTTG GGTGGCAGAA AAGCTGTTAA ACAGGGAGTG GTAAACCTTG TCAAATATGC      2820

CAAATAACAA CGGCAAGCAG ACAGAAGAGA AGAAGGGGGA TGGCCAGCCA GTCAATCAGC      2880

TGTGCCAGAT GCTGGGTAAG ATCATCGCTC AGCAAAACCA GTCCAGAGGC AAGGGACCGG      2940

GAAAGAAAAA TAAGAAGAAA AACCCGGAGA AGCCCCATTT TCCTCTAGCG ACTGAAGATG      3000

ATGTCAGACA TCACTTTACC CCTAGTGAGC GGCAATTGTG TCTGTCGTCA ATCCAGACCG      3060

CCTTTAATCA AGGCGCTGGG ACTTGCACCC TGTCAGATTC AGGGAGGATA AGTTACACTG      3120

TGGAGTTTAG TTTGCCTACG CATCATACTG TGCGCCTGAT CCGCGTCACA GCATCACCCT      3180

CAGCATGATG GGCTGGCATT CTTGAGGCAT CTCAGTGTTT GAATTGGAAG AATGTGTGGT      3240

GAATGGCACT GATTGACATT GTGCCTCTAA GTCACCTATT CAATTAGGGC GACCGTGTGG      3300

GGGTGAGATT TAATTGGCGA GAACCATGCG GCCGAAATTA AAAAAAAAAA AAAAAAA       3358
```

(2) INFORMATION FOR SEQ ID NO:2:

(i) SEQUENCE CHARACTERISTICS:
        (A) LENGTH: 768 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..768
        (C) IDENTIFICATION METHOD: experimental
        (D) OTHER INFORMATION: /evidence= EXPERIMENTAL
            /standard_name= "VR-2332 ORF 2"

(xi) SEQUENCE DESCRIPTION: SEQ ID NO:2:

```
ATG AAA TGG GGT CCA TGC AAA GCC TTT TTG ACA AAA TTG GCC AAC TTT        48
Met Lys Trp Gly Pro Cys Lys Ala Phe Leu Thr Lys Leu Ala Asn Phe
  1               5                  10                  15

TTG TGG ATG CTT TCA CGG AGT TCT TGG TGT CCA TTG TTG ATA TCA TTA        96
Leu Trp Met Leu Ser Arg Ser Ser Trp Cys Pro Leu Leu Ile Ser Leu
                 20                  25                  30

TAT TTT TGG CCA TTT TGT TTG GCT TCA CCA TCG CCG GTT GGC TGG TGG       144
Tyr Phe Trp Pro Phe Cys Leu Ala Ser Pro Ser Pro Val Gly Trp Trp
             35                  40                  45

TCT TTT GCA TCA GAT TGG TTT GCT CCG CGA TAC TCC GTA CGC GCC CTG       192
Ser Phe Ala Ser Asp Trp Phe Ala Pro Arg Tyr Ser Val Arg Ala Leu
 50                  55                  60

CCA TTC ACT CTG AGC AAT TAC AGA AGA TCT TAT GAG GCC TTT CTT TCC       240
Pro Phe Thr Leu Ser Asn Tyr Arg Arg Ser Tyr Glu Ala Phe Leu Ser
 65                  70                  75                  80

CAG TGC CAA GTG GAC ATT CCC ACC TGG GGA ACT AAA CAT CCT TTG GGG       288
Gln Cys Gln Val Asp Ile Pro Thr Trp Gly Thr Lys His Pro Leu Gly
                 85                  90                  95

ATG CTT TGG CAC CAT AAG GTG TCA ACC CTG ATT GAT GAA ATG GTG TCG       336
Met Leu Trp His His Lys Val Ser Thr Leu Ile Asp Glu Met Val Ser
            100                 105                 110

CGT CGA ATG TAC CGC ATC ATG GAA AAA GCA GGG CAG GCT GCC TGG AAA       384
Arg Arg Met Tyr Arg Ile Met Glu Lys Ala Gly Gln Ala Ala Trp Lys
                115                 120                 125

CAG GTG GTG AGC GAG GCT ACG CTG TCT CGC ATT AGT AGT TTG GAT GTG       432
Gln Val Val Ser Glu Ala Thr Leu Ser Arg Ile Ser Ser Leu Asp Val
130                 135                 140

GTG GCT CAT TTT CAG CAT CTA GCC GCC ATT GAA GCC GAG ACC TGT AAA       480
Val Ala His Phe Gln His Leu Ala Ala Ile Glu Ala Glu Thr Cys Lys
145                 150                 155                 160

TAT TTG GCC TCC CGG CTG CCC ATG CTA CAC AAC CTG CGC ATG ACA GGG       528
Tyr Leu Ala Ser Arg Leu Pro Met Leu His Asn Leu Arg Met Thr Gly
                165                 170                 175

TCA AAT GTA ACC ATA GTG TAT AAT AGC ACT TTG AAT CAG GTG TTT GCT       576
Ser Asn Val Thr Ile Val Tyr Asn Ser Thr Leu Asn Gln Val Phe Ala
            180                 185                 190

ATT TTT CCA ACC CCT GGT TCC CGG CCA AAG CTT CAT GAT TTT CAG CAA       624
Ile Phe Pro Thr Pro Gly Ser Arg Pro Lys Leu His Asp Phe Gln Gln
                195                 200                 205

TGG TTA ATA GCT GTA CAT TCC TCC ATA TTT TCC TCT GTT GCA GCT TCT       672
Trp Leu Ile Ala Val His Ser Ser Ile Phe Ser Ser Val Ala Ala Ser
210                 215                 220

TGT ACT CTT TTT GTT GTG CTG TGG TTG CGG GTT CCA ATA CTA CGT ACT       720
Cys Thr Leu Phe Val Val Leu Trp Leu Arg Val Pro Ile Leu Arg Thr
225                 230                 235                 240

GTT TTT GGT TTC CGC TGG TTA GGG GCA ATT TTT CTT TCG AAC TCA CAG       768
```

```
Val Phe Gly Phe Arg Trp Leu Gly Ala Ile Phe Leu Ser Asn Ser Gln
            245                 250                 255
```

(2) INFORMATION FOR SEQ ID NO:3:

(i) SEQUENCE CHARACTERISTICS:
        (A) LENGTH: 256 amino acids
        (B) TYPE: amino acid
        (D) TOPOLOGY: linear (ii) MOLECULE TYPE: protein (xi) SEQUENCE DESCRIPTION: SEQ ID NO:3:

```
Met Lys Trp Gly Pro Cys Lys Ala Phe Leu Thr Lys Leu Ala Asn Phe
 1                5                  10                  15
Leu Trp Met Leu Ser Arg Ser Ser Trp Cys Pro Leu Leu Ile Ser Leu
             20                  25                  30
Tyr Phe Trp Pro Phe Cys Leu Ala Ser Pro Ser Pro Val Gly Trp Trp
             35                  40                  45
Ser Phe Ala Ser Asp Trp Phe Ala Pro Arg Tyr Ser Val Arg Ala Leu
 50                  55                  60
Pro Phe Thr Leu Ser Asn Tyr Arg Arg Ser Tyr Glu Ala Phe Leu Ser
 65                  70                  75                  80
Gln Cys Gln Val Asp Ile Pro Thr Trp Gly Thr Lys His Pro Leu Gly
                 85                  90                  95
Met Leu Trp His His Lys Val Ser Thr Leu Ile Asp Glu Met Val Ser
            100                 105                 110
Arg Arg Met Tyr Arg Ile Met Glu Lys Ala Gly Gln Ala Ala Trp Lys
            115                 120                 125
Gln Val Val Ser Glu Ala Thr Leu Ser Arg Ile Ser Ser Leu Asp Val
130                 135                 140
Val Ala His Phe Gln His Leu Ala Ala Ile Glu Ala Glu Thr Cys Lys
145                 150                 155                 160
Tyr Leu Ala Ser Arg Leu Pro Met Leu His Asn Leu Arg Met Thr Gly
                165                 170                 175
Ser Asn Val Thr Ile Val Tyr Asn Ser Thr Leu Asn Gln Val Phe Ala
            180                 185                 190
Ile Phe Pro Thr Pro Gly Ser Arg Pro Lys Leu His Asp Phe Gln Gln
            195                 200                 205
Trp Leu Ile Ala Val His Ser Ser Ile Phe Ser Ser Val Ala Ala Ser
210                 215                 220
Cys Thr Leu Phe Val Val Leu Trp Leu Arg Val Pro Ile Leu Arg Thr
225                 230                 235                 240
Val Phe Gly Phe Arg Trp Leu Gly Ala Ile Phe Leu Ser Asn Ser Gln
                245                 250                 255
```

(2) INFORMATION FOR SEQ ID NO:4:

(i) SEQUENCE CHARACTERISTICS:
        (A) LENGTH: 762 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..762
        (C) IDENTIFICATION METHOD: experimental
        (D) OTHER INFORMATION: /evidence= EXPERIMENTAL
            /standard_name= "VR-2332 ORF 3"

(xi) SEQUENCE DESCRIPTION: SEQ ID NO:4:

```
ATG GTT AAT AGC TGT ACA TTC CTC CAT ATT TTC CTC TGT TGC AGC TTC      48
Met Val Asn Ser Cys Thr Phe Leu His Ile Phe Leu Cys Cys Ser Phe
 1               5                  10                  15

TTG TAC TCT TTT TGT TGT GCT GTG GTT GCG GGT TCC AAT ACT ACG TAC      96
Leu Tyr Ser Phe Cys Cys Ala Val Val Ala Gly Ser Asn Thr Thr Tyr
             20                  25                  30

TGT TTT TGG TTT CCG CTG GTT AGG GGC AAT TTT TCT TTC GAA CTC ACA     144
Cys Phe Trp Phe Pro Leu Val Arg Gly Asn Phe Ser Phe Glu Leu Thr
         35                  40                  45

GTG AAT TAC ACG GTG TGT CCA CCT TGC CTC ACC CGG CAA GCA GCC ACA     192
Val Asn Tyr Thr Val Cys Pro Pro Cys Leu Thr Arg Gln Ala Ala Thr
     50                  55                  60

GAG ATC TAC GAA CCC GGT AGG TCT CTT TGG TGC AGG ATA GGG TAT GAC     240
Glu Ile Tyr Glu Pro Gly Arg Ser Leu Trp Cys Arg Ile Gly Tyr Asp
 65                  70                  75                  80

CGA TGT GGG GAG GAC GAT CAT GAC GAG CTA GGG TTT ATG ATA CCG CCT     288
Arg Cys Gly Glu Asp Asp His Asp Glu Leu Gly Phe Met Ile Pro Pro
                 85                  90                  95

GGC CTC TCC AGC GAA GGC CAC TTG ACT GGT GTT TAC GCC TGG TTG GCG     336
Gly Leu Ser Ser Glu Gly His Leu Thr Gly Val Tyr Ala Trp Leu Ala
            100                 105                 110

TTC TTG TCC TTC AGC TAC ACG GCC CAG TTC CAT CCC GAG ATA TTC GGG     384
Phe Leu Ser Phe Ser Tyr Thr Ala Gln Phe His Pro Glu Ile Phe Gly
        115                 120                 125

ATA GGG AAT GTG AGT CGA GTT TAT GTT GAC ATC AAA CAT CAA CTC ATC     432
Ile Gly Asn Val Ser Arg Val Tyr Val Asp Ile Lys His Gln Leu Ile
    130                 135                 140

TGC GCC GAA CAT GAC GGG CAG AAC ACC ACC TTG CCT CGT CAT GAC AAC     480
Cys Ala Glu His Asp Gly Gln Asn Thr Thr Leu Pro Arg His Asp Asn
145                 150                 155                 160

ATT TCA GCC GTG TTT CAG ACC TAT TAC CAA CAT CAA GTC GAC GGC GGC     528
Ile Ser Ala Val Phe Gln Thr Tyr Tyr Gln His Gln Val Asp Gly Gly
                165                 170                 175

AAT TGG TTT CAC CTA GAA TGG CTT CGT CCC TTC TTT TCC TCG TGG TTG     576
Asn Trp Phe His Leu Glu Trp Leu Arg Pro Phe Phe Ser Ser Trp Leu
            180                 185                 190

GTT TTA AAT GTC TCT TGG TTT CTC AGG CGT TCG CCT GCA AAC CAT GTT     624
Val Leu Asn Val Ser Trp Phe Leu Arg Arg Ser Pro Ala Asn His Val
        195                 200                 205

TCA GTT CGA GTC TTG CAG ATA TTA AGA CCA ACA CCA CCG CAG CGG CAA     672
Ser Val Arg Val Leu Gln Ile Leu Arg Pro Thr Pro Pro Gln Arg Gln
    210                 215                 220

GCT TTG CTG TCC TCC AAG ACA TCA GTT GCC TTA GGC ATC GCG ACT CGG     720
Ala Leu Leu Ser Ser Lys Thr Ser Val Ala Leu Gly Ile Ala Thr Arg
225                 230                 235                 240

CCT CTG AGG CGA TTC GCA AAA TCC CTC AGT GCC GTA CGG CGA             762
Pro Leu Arg Arg Phe Ala Lys Ser Leu Ser Ala Val Arg Arg
                245                 250
```

(2) INFORMATION FOR SEQ ID NO:5:

(i) SEQUENCE CHARACTERISTICS:
      (A) LENGTH: 254 amino acids
      (B) TYPE: amino acid
      (D) TOPOLOGY: linear (ii) MOLECULE TYPE: protein (xi) SEQUENCE DESCRIPTION: SEQ ID NO:5:

Met Val Asn Ser Cys Thr Phe Leu His Ile Phe Leu Cys Cys Ser Phe

```
                1               5                   10                      15
        Leu Tyr Ser Phe Cys Cys Ala Val Val Ala Gly Ser Asn Thr Thr Tyr
                        20                  25                  30

Cys Phe Trp Phe Pro Leu Val Arg Gly Asn Phe Ser Phe Glu Leu Thr
                        35                  40                  45

Val Asn Tyr Thr Val Cys Pro Pro Cys Leu Thr Arg Gln Ala Ala Thr
                        50                  55                  60

Glu Ile Tyr Glu Pro Gly Arg Ser Leu Trp Cys Arg Ile Gly Tyr Asp
        65                      70                  75                      80

Arg Cys Gly Glu Asp Asp His Asp Glu Leu Gly Phe Met Ile Pro Pro
                            85                  90                  95

Gly Leu Ser Ser Glu Gly His Leu Thr Gly Val Tyr Ala Trp Leu Ala
                        100                 105                 110

Phe Leu Ser Phe Ser Tyr Thr Ala Gln Phe His Pro Glu Ile Phe Gly
                        115                 120                 125

Ile Gly Asn Val Ser Arg Val Tyr Val Asp Ile Lys His Gln Leu Ile
                        130                 135                 140

Cys Ala Glu His Asp Gly Gln Asn Thr Thr Leu Pro Arg His Asp Asn
        145                     150                 155                 160

Ile Ser Ala Val Phe Gln Thr Tyr Tyr Gln His Gln Val Asp Gly Gly
                        165                 170                 175

Asn Trp Phe His Leu Glu Trp Leu Arg Pro Phe Phe Ser Ser Trp Leu
                        180                 185                 190

Val Leu Asn Val Ser Trp Phe Leu Arg Arg Ser Pro Ala Asn His Val
                        195                 200                 205

Ser Val Arg Val Leu Gln Ile Leu Arg Pro Thr Pro Pro Gln Arg Gln
                        210                 215                 220

Ala Leu Leu Ser Ser Lys Thr Ser Val Ala Leu Gly Ile Ala Thr Arg
        225                     230                 235                 240

Pro Leu Arg Arg Phe Ala Lys Ser Leu Ser Ala Val Arg Arg
                        245                 250

(2) INFORMATION FOR SEQ ID NO:6:

(i) SEQUENCE CHARACTERISTICS:
        (A) LENGTH: 534 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..534
        (C) IDENTIFICATION METHOD: experimental
        (D) OTHER INFORMATION: /evidence= EXPERIMENTAL
            /standard_name= "VR-2332 ORF 4"

(xi) SEQUENCE DESCRIPTION: SEQ ID NO:6:

ATG GCT TCG TCC CTT CTT TTC CTC GTG GTT GGT TTT AAA TGT CTC TTG        48
Met Ala Ser Ser Leu Leu Phe Leu Val Val Gly Phe Lys Cys Leu Leu
  1               5                   10                  15

GTT TCT CAG GCG TTC GCC TGC AAA CCA TGT TTC AGT TCG AGT CTT GCA        96
Val Ser Gln Ala Phe Ala Cys Lys Pro Cys Phe Ser Ser Ser Leu Ala
                20                  25                  30

GAT ATT AAG ACC AAC ACC ACC GCA GCG GCA AGC TTT GCT GTC CTC CAA       144
Asp Ile Lys Thr Asn Thr Thr Ala Ala Ala Ser Phe Ala Val Leu Gln
                35                  40                  45

GAC ATC AGT TGC CTT AGG CAT CGC GAC TCG GCC TCT GAG GCG ATT CGC       192
```

```
Asp Ile Ser Cys Leu Arg His Arg Asp Ser Ala Ser Glu Ala Ile Arg
    50                  55                  60

AAA ATC CCT CAG TGC CGT ACG GCG ATA GGG ACA CCC GTG TAT GTT ACC      240
Lys Ile Pro Gln Cys Arg Thr Ala Ile Gly Thr Pro Val Tyr Val Thr
65                  70                  75                  80

ATC ACA GCC AAT GTG ACA GAT GAG AAT TAT TTA CAT TCT TCT GAT CTC      288
Ile Thr Ala Asn Val Thr Asp Glu Asn Tyr Leu His Ser Ser Asp Leu
            85                  90                  95

CTC ATG CTT TCT TCT TGC CTT TTC TAT GCT TCT GAG ATG AGT GAA AAG      336
Leu Met Leu Ser Ser Cys Leu Phe Tyr Ala Ser Glu Met Ser Glu Lys
                100                 105                 110

GGA TTT AAG GTG GTA TTT GGC AAT GTG TCA GGC ATC GTG GCT GTG TGT      384
Gly Phe Lys Val Val Phe Gly Asn Val Ser Gly Ile Val Ala Val Cys
                115                 120                 125

GTC AAT TTT ACC AGC TAC GTC CAA CAT GTC AAG GAG TTT ACC CAA CGC      432
Val Asn Phe Thr Ser Tyr Val Gln His Val Lys Glu Phe Thr Gln Arg
        130                 135                 140

TCC CTG GTG GTC GAC CAT GTG CGG TTG CTC CAT TTC ATG ACA CCT GAG      480
Ser Leu Val Val Asp His Val Arg Leu Leu His Phe Met Thr Pro Glu
145                 150                 155                 160

ACC ATG AGG TGG GCA ACT GTT TTA GCC TGT CTT TTT GCC ATT CTG TTG      528
Thr Met Arg Trp Ala Thr Val Leu Ala Cys Leu Phe Ala Ile Leu Leu
                165                 170                 175

GCA ATT                                                              534
Ala Ile
```

(2) INFORMATION FOR SEQ ID NO:7:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO:7:

```
Met Ala Ser Ser Leu Leu Phe Leu Val Val Gly Phe Lys Cys Leu Leu
1               5                   10                  15

Val Ser Gln Ala Phe Ala Cys Lys Pro Cys Phe Ser Ser Ser Leu Ala
                20                  25                  30

Asp Ile Lys Thr Asn Thr Thr Ala Ala Ser Phe Ala Val Leu Gln
            35                  40                  45

Asp Ile Ser Cys Leu Arg His Arg Asp Ser Ala Ser Glu Ala Ile Arg
    50                  55                  60

Lys Ile Pro Gln Cys Arg Thr Ala Ile Gly Thr Pro Val Tyr Val Thr
65                  70                  75                  80

Ile Thr Ala Asn Val Thr Asp Glu Asn Tyr Leu His Ser Ser Asp Leu
            85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
                115                 120                 125

Val Asn Phe Thr Ser Tyr Val Gln His Val Lys Glu Phe Thr Gln Arg
        130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile
```

(2) INFORMATION FOR SEQ ID NO:8:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..600
        (C) IDENTIFICATION METHOD: experimental
        (D) OTHER INFORMATION: /evidence= EXPERIMENTAL
            /standard_name= "VR-2332 ORF5"

(xi) SEQUENCE DESCRIPTION: SEQ ID NO:8:

```
ATG TTG GAG AAA TGC TTG ACC GCG GGC TGT TGC TCG CG (ii) MOLECULE TYPE: protein (xi) SEQUENCE DESCRIPTION: SEQ ID NO:9:

```
Met Leu Glu Lys Cys Leu Thr Ala Gly Cys Cys Ser Arg Leu Leu Ser
 1               5                  10                  15

Leu Trp Cys Ile Val Pro Phe Cys Phe Ala Val Leu Ala Asn Ala Ser
                20                  25                  30

Asn Asp Ser Ser Ser His Leu Gln Leu Ile Tyr Asn Leu Thr Leu Cys
                35                  40                  45

Glu Leu Asn Gly Thr Asp Trp Leu Ala Asn Lys Phe Asp Trp Ala Val
     50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                    85                  90                  95

Ser Thr Ala Gly Phe Val His Gly Arg Tyr Val Leu Ser Ser Ile Tyr
                100                 105                 110

Ala Val Cys Ala Leu Ala Ala Leu Thr Cys Phe Val Ile Arg Phe Ala
                115                 120                 125

Lys Asn Cys Met Ser Trp Arg Tyr Ala Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
                180                 185                 190

Ser Ala Glu Gln Trp Gly Arg Pro
                195                 200
```

(2) INFORMATION FOR SEQ ID NO:10:

(i) SEQUENCE CHARACTERISTICS:
        (A) LENGTH: 522 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..522
        (C) IDENTIFICATION METHOD: experimental
        (D) OTHER INFORMATION: /evidence= EXPERIMENTAL
            /standard_name= "VR-2332 ORF 6"

(xi) SEQUENCE DESCRIPTION: SEQ ID NO:10:

```
ATG GGG TCG TCC TTA GAT GAC TTC TGT CAT GAT AGC ACG GCT CCA CAA      48
Met Gly Ser Ser Leu Asp Asp Phe Cys His Asp Ser Thr Ala Pro Gln
 1               5                  10                  15

AAG GTG CTT TTG GCG TTT TCT ATT ACC TAC ACG CCA GTG ATG ATA TAT      96
Lys Val Leu Leu Ala Phe Ser Ile Thr Tyr Thr Pro Val Met Ile Tyr
                20                  25                  30

GCC CTA AAG GTG AGT CGC GGC CGA CTG CTA GGG CTT CTG CAC CTT TTG     144
Ala Leu Lys Val Ser Arg Gly Arg Leu Leu Gly Leu Leu His Leu Leu
                35                  40                  45

ATC TTC CTG AAT TGT GCT TTC ACC TTC GGG TAC ATG ACT TTC GCG CAC     192
Ile Phe Leu Asn Cys Ala Phe Thr Phe Gly Tyr Met Thr Phe Ala His
     50                  55                  60
```

```
TTT CAG AGT ACA AAT AAG GTC GCG CTC ACT ATG GGA GCA GTA GTT GCA        240
Phe Gln Ser Thr Asn Lys Val Ala Leu Thr Met Gly Ala Val Val Ala
 65                  70                  75                  80

CTC CTT TGG GGG GTG TAC TCA GCC ATA GAA ACC TGG AAA TTC ATC ACC        288
Leu Leu Trp Gly Val Tyr Ser Ala Ile Glu Thr Trp Lys Phe Ile Thr
                 85                  90                  95

TCC AGA TGC CGT TTG TGC TTG CTA GGC CGC AAG TAC ATT CTG GCC CCT        336
Ser Arg Cys Arg Leu Cys Leu Leu Gly Arg Lys Tyr Ile Leu Ala Pro
            100                 105                 110

GCC CAC CAC GTT GAA AGT GCC GCA CGG TTT CAT CCG ATT GCG GCA AAT        384
Ala His His Val Glu Ser Ala Ala Arg Phe His Pro Ile Ala Ala Asn
        115                 120                 125

GAT AAC CAC GCA TTT GTC GTC CGG CGT CCC GGC TCC ACT ACG GTC AAC        432
Asp Asn His Ala Phe Val Val Arg Arg Pro Gly Ser Thr Thr Val Asn
    130                 135                 140

GGC ACA TTG GTG CCC GGG TTA AAA AGC CTC GTG TTG GGT GGC AGA AAA        480
Gly Thr Leu Val Pro Gly Leu Lys Ser Leu Val Leu Gly Gly Arg Lys
145                 150                 155                 160

GCT GTT AAA CAG GGA GTG GTA AAC CTT GTC AAA TAT GCC AAA                522
Ala Val Lys Gln Gly Val Val Asn Leu Val Lys Tyr Ala Lys
                165                 170
```

(2) INFORMATION FOR SEQ ID NO:11:

(i) SEQUENCE CHARACTERISTICS:
        (A) LENGTH: 174 amino acids
        (B) TYPE: amino acid
        (D) TOPOLOGY: linear (ii) MOLECULE TYPE: protein (xi) SEQUENCE DESCRIPTION: SEQ ID NO:11:

```
Met Gly Ser Ser Leu Asp Asp Phe Cys His Asp Ser Thr Ala Pro Gln
 1               5                  10                  15

Lys Val Leu Leu Ala Phe Ser Ile Thr Tyr Thr Pro Val Met Ile Tyr
             20                  25                  30

Ala Leu Lys Val Ser Arg Gly Arg Leu Leu Gly Leu Leu His Leu Leu
         35                  40                  45

Ile Phe Leu Asn Cys Ala Phe Thr Phe Gly Tyr Met Thr Phe Ala His
     50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Arg Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170
```

(2) INFORMATION FOR SEQ ID NO:12:

(i) SEQUENCE CHARACTERISTICS:
        (A) LENGTH: 369 base pairs
        (B) TYPE: nucleic acid
        (C) STRANDEDNESS: double (D) TOPOLOGY: linear (ii) MOLECULE TYPE: cDNA (ix) FEATURE:
         (A) NAME/KEY: CDS
         (B) LOCATION: 1..369
         (C) IDENTIFICATION METHOD: experimental
         (D) OTHER INFORMATION: /evidence= EXPERIMENTAL
             /standard_name= "VR-2332 ORF 7"

(xi) SEQUENCE DESCRIPTION: SEQ ID NO:12:

```
ATG CCA AAT AAC AAC GGC AAG CAG ACA GAA GAG AAG AAG GGG GAT GGC      48
Met Pro Asn Asn Asn Gly Lys Gln Thr Glu Glu Lys Lys Gly Asp Gly
 1               5                  10                  15

CAG CCA GTC AAT CAG CTG TGC CAG ATG CTG GGT AAG ATC ATC GCT CAG      96
Gln Pro Val Asn Gln Leu Cys Gln Met Leu Gly Lys Ile Ile Ala Gln
             20                  25                  30

CAA AAC CAG TCC AGA GGC AAG GGA CCG GGA AAG AAA AAT AAG AAG AAA     144
Gln Asn Gln Ser Arg Gly Lys Gly Pro Gly Lys Lys Asn Lys Lys Lys
         35                  40                  45

AAC CCG GAG AAG CCC CAT TTT CCT CTA GCG ACT GAA GAT GAT GTC AGA     192
Asn Pro Glu Lys Pro His Phe Pro Leu Ala Thr Glu Asp Asp Val Arg
 50                  55                  60

CAT CAC TTT ACC CCT AGT GAG CGG CAA TTG TGT CTG TCG TCA ATC CAG     240
His His Phe Thr Pro Ser Glu Arg Gln Leu Cys Leu Ser Ser Ile Gln
 65                  70                  75                  80

ACC GCC TTT AAT CAA GGC GCT GGG ACT TGC ACC CTG TCA GAT TCA GGG     288
Thr Ala Phe Asn Gln Gly Ala Gly Thr Cys Thr Leu Ser Asp Ser Gly
             85                  90                  95

AGG ATA AGT TAC ACT GTG GAG TTT AGT TTG CCT ACG CAT CAT ACT GTG     336
Arg Ile Ser Tyr Thr Val Glu Phe Ser Leu Pro Thr His His Thr Val
             100                 105                 110

CGC CTG ATC CGC GTC ACA GCA TCA CCC TCA GCA                         369
Arg Leu Ile Arg Val Thr Ala Ser Pro Ser Ala
         115                 120
```

(2) INFORMATION FOR SEQ ID NO:13:

(i) SEQUENCE CHARACTERISTICS:
        (A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO:13:

```
Met Pro Asn Asn Asn Gly Lys Gln Thr Glu Glu Lys Lys Gly Asp Gly
 1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
 50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
             85                  90                  95

Arg Ile Ser Tyr Thr Val Glu Phe Ser Leu Pro Thr His His Thr Val
             100                 105                 110

Arg Leu Ile Arg Val Thr Ala Ser Pro Ser Ala
         115                 120
```

(2) INFORMATION FOR SEQ ID NO:14:

(i) SEQUENCE CHARACTERISTICS:
       (A) LENGTH: 15101 base pairs
       (B) TYPE: nucleic acid
       (C) STRANDEDNESS: double
       (D) TOPOLOGY: unknown (ii) MOLECULE TYPE: cDNA (iii) HYPOTHETICAL: NO (iv) ANTI-SENSE: NO (vi) ORIGINAL SOURCE:
       (A) ORGANISM: Arteriviridae
       (B) STRAIN: VR-2332

(ix) FEATURE:
       (A) NAME/KEY: misc_feature
       (B) LOCATION: 7384..11775
       (C) IDENTIFICATION METHOD: experimental
       (D) OTHER INFORMATION: /evidence= EXPERIMENTAL
/label= ORF1b
/citation= ([1])

(ix) FEATURE:
(A) NAME/KEY: misc_feature
(B) LOCATION: 11786..12535
(D) OTHER INFORMATION: /standard_name= "LV ORF 2"
/citation= ([1])

(ix) FEATURE:
(A) NAME/KEY: misc_feature
(B) LOCATION: 212..7402
(D) OTHER INFORMATION: /standard_name= "LV ORF 1a"
/citation= ([1])

(ix) FEATURE:
(A) NAME/KEY: misc_feature
(B) LOCATION: 12394..13191
(D) OTHER INFORMATION: /standard_name= "LV ORF 3"
/citation= ([1])

(ix) FEATURE:
(A) NAME/KEY: misc_feature
(B) LOCATION: 12936..13487
(D) OTHER INFORMATION: /standard_name= "LV ORF 4"
/citation= ([1])

(ix) FEATURE:
(A) NAME/KEY: misc_feature
(B) LOCATION: 13484..14089
(D) OTHER INFORMATION: /standard_name= "LV ORF 5"
/citation= ([1])

(ix) FEATURE:
(A) NAME/KEY: misc_feature
(B) LOCATION: 14077..14598
(D) OTHER INFORMATION: /standard_name= "LV ORF 6"
/citation= ([1])

(ix) FEATURE:
(A) NAME/KEY: misc_feature
(B) LOCATION: 14588..14974
(D) OTHER INFORMATION: /standard_name= "LV ORF 7"
/citation= ([1])

(x) PUBLICATION INFORMATION:
(A) AUTHORS: Meulenberg, J. J.M.
Hulst, M. M.
de Veijer, E. J.
Moonen, P. L.
den Besten, A.
de Kluyver, E. P.
Wensvoort, G.
Moormann, R. J.
(B) TITLE: Lelystad virus, the causative agent of procine epidemic abnortion and respiratory
syndrome (PEARS) is related to LDV and EAV.
(C) JOURNAL: Virology
(D) VOLUME: 192
(F) PAGES: 62-72
(G) DATE: 1993
(K) RELEVANT RESIDUES IN SEQ ID NO:14: FROM 1 TO 15101

(xi) SEQUENCE DESCRIPTION: SEQ ID NO:14:

```
GGGTATTCCC CCTACATACA CGACACTTCT AGTGTTTGTG TACCTTGGAG GCGTGGGTAC      60

AGCCCCGCCC CACCCCTTGG CCCCTGTTCT AGCCCAACAG GTATCCTTCT CTCTCGGGGC     120

GAGTGCGCCG CCTGCTGCTC CCTTGCAGCG GGAAGGACCT CCCGAGTATT TCCGGAGAGC     180

ACCTGCTTTA CGGGATCTCC ACCCTTTAAC CATGTCTGGG ACGTTCTCCC GGTGCATGTG     240

CACCCCGGCT GCCCGGGTAT TTTGGAACGC CGGCCAAGTC TTTTGCACAC GGTGTCTCAG     300

TGCGCGGTCT CTTCTCTCTC CAGAGCTTCA GGACACTGAC CTCGGTGCAG TTGGCTTGTT     360

TTACAAGCCT AGGGACAAGC TTCACTGGAA AGTCCCTATC GGCATCCCTC AGGTGGAATG     420

TACTCCATCC GGGTGCTGTT GGCTCTCAGC TGTTTTCCCT TTGGCGCGTA TGACCTCCGG     480

CAATCACAAC TTCCTCCAAC GACTTGTGAA GGTTGCTGAT GTTTTGTACC GTGACGGTTG     540

CTTGGCACCT CGACACCTTC GTGAACTCCA AGTTTACGAG CGCGGCTGCA ACTGGTACCC     600

GATCACGGGG CCCGTGCCCG GGATGGGTTT GTTTGCGAAC TCCATGCACG TATCCGACCA     660

GCCGTTCCCT GGTGCCACCC ATGTGTTGAC TAACTCGCCT TTGCCTCAAC AGGCTTGTCG     720

GCAGCCGTTC TGTCCATTTG AGGAGGCTCA TTCTAGCGTG TACAGGTGGA AGAAATTTGT     780

GGTTTTCACG GACTCCTCCC TCAACGGTCG ATCTCGCATG ATGTGGACGC CGGAATCCGA     840

TGATTCAGCC GCCCTGGAGG TACTACCGCC TGAGTTAGAA CGTCAGGTCG AAATCCTCAT     900

TCGGAGTTTT CCTGCTCATC ACCCTGTCGA CCTGGCCGAC TGGGAGCTCA CTGAGTCCCC     960

TGAGAACGGT TTTTCCTTCA ACACGTCTCA TTCTTGCGGT CACCTTGTCC AGAACCCCGA    1020

CGTGTTTGAT GGCAAGTGCT GGCTCTCCTG CTTTTTGGGC CAGTCGGTCG AAGTGCGCTG    1080

CCATGAGGAA CATCTAGCTG ACGCCTTCGG TTACCAAACC AAGTGGGGCG TGCATGGTAA    1140

GTACCTCCAG CGCAGGCTTC AAGTTCGCGG CATTCGTGCT GTAGTCGATC CTGATGGTCC    1200

CATTCACGTT GAAGCGCTGT CTTGCCCCCA GTCTTGGATC AGGCACCTGA CTCTGGATGA    1260

TGATGTCACC CCAGGATTCG TTCGCCTGAC ATCCCTTCGC ATTGTGCCGA ACACAGAGCC    1320

TACCACTTCC CGGATCTTTC GGTTTGGAGC GCATAAGTGG TATGGCGCTG CCGGCAAACG    1380

GGCTCGTGCT AAGCGTGCCG CTAAAAGTGA AAGGATTCG GCTCCCACCC CAAGGTTGC     1440

CCTGCCGGTC CCCACCTGTG GAATTACCAC CTACTCTCCA CCGACAGACG GGTCTTGTGG    1500

TTGGCATGTC CTTGCCGCCA TAATGAACCG GATGATAAAT GGTGACTTCA CGTCCCCTCT    1560

GACTCAGTAC AACAGACCAG AGGATGATTG GGCTTCTGAT TATGATCTTG TTCAGGCGAT    1620

TCAATGTCTA CGACTGCCTG CTACCGTGGT TCGGAATCGC GCCTGTCCTA ACGCCAAGTA    1680

CCTTATAAAA CTTAACGGAG TTCACTGGGA GGTAGAGGTG AGGTCTGGAA TGGCTCCTCG    1740

CTCCCTTTCT CGTGAATGTG TGGTTGGCGT TTGCTCTGAA GGCTGTGTCG CACCGCCTTA    1800

TCCAGCAGAC GGGCTACCTA AACGTGCACT CGAGGCCTTG GCGTCTGCTT ACAGACTACC    1860

CTCCGATTGT GTTAGCTCTG GTATTGCTGA CTTTCTTGCT AATCCACCTC CTCAGGAATT    1920

CTGGACCCTC GACAAAATGT TGACCTCCCC GTCACCAGAG CGGTCCGGCT TCTCTAGTTT    1980

GTATAAATTA CTATTAGAGG TTGTTCCGCA AAAATGCGGT GCCACGGAAG GGCTTTCAT    2040

CTATGCTGTT GAGAGGATGT TGAAGGATTG TCCGAGCTCC AAACAGGCCA TGGCCCTTCT    2100
```

```
GGCAAAAATT AAAGTTCCAT CCTCAAAGGC CCCGTCTGTG TCCCTGGACG AGTGTTTCCC    2160

TACGGATGTT TTAGCCGACT TCGAGCCAGC ATCTCAGGAA AGGCCCCAAA GTTCCGGCGC    2220

TGCTGTTGTC CTGTGTTCAC CGGATGCAAA AGAGTTCGAG GAAGCAGCCC CGGAAGAAGT    2280

TCAAGAGAGT GGCCACAAGG CCGTCCACTC TGCACTCCTT GCCGAGGGTC CTAACAATGA    2340

GCAGGTACAG GTGGTTGCCG GTGAGCAACT GAAGCTCGGC GGTTGTGGTT TGGCAGTCGG    2400

GAATGCTCAT GAAGGTGCTC TGGTCTCAGC TGGTCTAATT AACCTGGTAG GCGGGAATTT    2460

GTCCCCCTCA GACCCCATGA AAGAAAACAT GCTCAATAGC CGGGAAGACG AACCACTGGA    2520

TTTGTCCCAA CCAGCACCAG CTTCCACAAC GACCCTTGTG AGAGAGCAAA CACCCGACAA    2580

CCCAGGTTCT GATGCCGGTG CCCTCCCCGT CACCGTTCGA GAATTTGTCC CGACGGGGCC    2640

TATACTCTGT CATGTTGAGC ACTGCGGCAC GGAGTCGGGC GACAGCAGTT CGCCTTTGGA    2700

TCTATCTGAT GCGCAAACCC TGGACCAGCC TTTAAATCTA TCCCTGGCCG CTTGGCCAGT    2760

GAGGGCCACC GCGTCTGACC CTGGCTGGGT CCACGGTAGG CGCGAGCCTG TCTTTGTAAA    2820

GCCTCGAAAT GCTTTCTCTG ATGGCGATTC AGCCCTTCAG TTCGGGGAGC TTTCTGAATC    2880

CAGCTCTGTC ATCGAGTTTG ACCGGACAAA AGATGCTCCG GTGGTTGACG CCCCTGTCGA    2940

CTTGACGACT TCGAACGAGG CCCTCTCTGT AGTCGATCCT TTCGAATTTG CCGAACTCAA    3000

GCGCCCGCGT TTCTCCGCAC AAGCCTTAAT TGACCGAGGC GGTCCACTTG CCGATGTCCA    3060

TGCAAAAATA AAGAACCGGG TATATGAACA GTGCCTCCAA GCTTGTGAGC CCGGTAGTCG    3120

TGCAACCCCA GCCACCAGGG AGTGGCTCGA CAAAATGTGG GATAGGGTGG ACATGAAAAC    3180

TTGGCGCTGC ACCTCGCAGT TCCAAGCTGG TCGCATTCTT GCGTCCCTCA AATTCCTCCC    3240

TGACATGATT CAAGACACAC CGCCTCCTGT TCCCAGGAAG AACCGAGCTA GTGACAATGC    3300

CGGCCTGAAG CAACTGGTGG CACAGTGGGA TAGGAAATTG AGTGTGACCC CCCCCCCAAA    3360

ACCGGTTGGG CCAGTGCTTG ACCAGATCGT CCCTCCGCCT ACGGATATCC AGCAAGAAGA    3420

TGTCACCCCC TCCGATGGGC CACCCCATGC GCCGGATTTT CCTAGTCGAG TGAGCACGGG    3480

CGGGAGTTGG AAAGGCCTTA TGCTTTCCGG CACCCGTCTC GCGGGGTCTA TCAGCCAGCG    3540

CCTTATGACA TGGGTTTTTG AAGTTTTCTC CCACCTCCCA GCTTTTATGC TCACACTTTT    3600

CTCGCCGCGG GGCTCTATGG CTCCAGGTGA TTGGTTGTTT GCAGGTGTCG TTTTACTTGC    3660

TCTCTTGCTC TGTCGTTCTT ACCCGATACT CGGATGCCTT CCCTTATTGG GTGTCTTTTC    3720

TGGTTCTTTG CGGCGTGTTC GTCTGGGTGT TTTTGGTTCT TGGATGGCTT TTGCTGTATT    3780

TTTATTCTCG ACTCCATCCA ACCCAGTCGG TTCTTCTTGT GACCACGATT CGCCGGAGTG    3840

TCATGCTGAG CTTTTGGCTC TTGAGCAGCG CCAACTTTGG GAACCTGTGC GCGGCCTTGT    3900

GGTCGGCCCC TCAGGCCTCT TATGTGTCAT TCTTGGCAAG TTACTCGGTG GGTCACGTTA    3960

TCTCTGGCAT GTTCTCCTAC GTTTATGCAT GCTTGCAGAT TTGGCCCTTT CTCTTGTTTA    4020

TGTGGTGTCC CAGGGGCGTT GTCACAAGTG TTGGGGAAAG TGTATAAGGA CAGCTCCTGC    4080

GGAGGTGGCT CTTAATGTAT TTCCTTTCTC GCGCGCCACC CGTGTCTCTC TTGTATCCTT    4140

GTGTGATCGA TTCCAAACGC CAAAAGGGGT TGATCCTGTG CACTTGGCAA CGGGTTGGCG    4200

CGGGTGCTGG CGTGGTGAGA GCCCCATCCA TCAACCACAC CAAAAGCCCA TAGCTTATGC    4260

CAATTTGGAT GAAAAGAAAA TGTCTGCCCA AACGGTGGTT GCTGTCCCAT ACGATCCCAG    4320

TCAGGCTATC AAATGCCTGA AAGTTCTGCA GGCGGGAGGG GCCATCGTGG ACCAGCCTAC    4380

ACCTGAGGTC GTTCGTGTGT CCGAGATCCC CTTCTCAGCC CCATTTTTCC CAAAAGTTCC    4440

AGTCAACCCA GATTGCAGGG TTGTGGTAGA TTCGGACACT TTTGTGGCTG CGGTTCGCTG    4500
```

```
CGGTTACTCG ACAGCACAAC TGGTTCTGGG CCGGGGCAAC TTTGCCAAGT TAAATCAGAC    4560

CCCCCCCAGG AACTCTATCT CCACCAAAAC GACTGGTGGG GCCTCTTACA CCCTTGCTGT    4620

GGCTCAAGTG TCTGCGTGGA CTCTTGTTCA TTTCATCCTC GGTCTTTGGT TCACATCACC    4680

TCAAGTGTGT GGCCGAGGAA CCGCTGACCC ATGGTGTTCA AATCCTTTTT CATATCCTAC    4740

CTATGGCCCC GGAGTTGTGT GCTCCTCTCG ACTTTGTGTG TCTGCCGACG GGTCACCCT     4800

GCCATTGTTC TCAGCCGTGG CACAACTCTC CGGTAGAGAG GTGGGGATTT TTATTTTGGT    4860

GCTCGTCTCC TTGACTGCTT TGGCCCACCG CATGGCTCTT AAGGCAGACA TGTTAGTGGT    4920

CTTTTCGGCT TTTTGTGCTT ACGCCTGGCC CATGAGCTCC TGGTTAATCT GCTTCTTTCC    4980

TATACTCTTG AAGTGGGTTA CCCTTCACCC TCTTACTATG CTTTGGGTGC ACTCATTCTT    5040

GGTGTTTTGT CTGCCAGCAG CCGGCATCCT CTCACTAGGG ATAACTGGCC TTCTTTGGGC    5100

AATTGGCCGC TTTACCCAGG TTGCCGGAAT TATTACACCT TATGCATCC ACCAGTACAC     5160

CTCTGGGCCA CGTGGTGCAG CTGCTGTGGC CACAGCCCCA GAAGGCACTT ATATGGCCGC    5220

CGTCCGGAGA GCTGCTTTAA CTGGGCGAAC TTTAATCTTC ACCCCGTCTG CAGTTGGATC    5280

CCTTCTCGAA GGTGCTTTCA GGACTCATAA ACCCTGCCTT AACACCGTGA ATGTTGTAGG    5340

CTCTTCCCTT GGTTCCGGAG GGGTTTTCAC CATTGATGGC AGAAGAACTG TCGTCACTGC    5400

TGCCCATGTG TTGAACGGCG ACACAGCTAG AGTCACCGGC GACTCCTACA ACCGCATGCA    5460

CACTTTCAAG ACCAATGGTG ATTATGCCTG GTCCCATGCT GATGACTGGC AGGGCGTTGC    5520

CCCTGTGGTC AAGGTTGCGA AGGGGTACCG CGGTCGTGCC TACTGGCAAA CATCAACTGG    5580

TGTCGAACCC GGTATCATTG GGAAGGGTT CGCCTTCTGT TTTACTAACT GCGGCGATTC     5640

GGGGTCACCC GTCATCTCAG AATCTGGTGA TCTTATTGGA ATCCACACCG GTTCAAACAA    5700

ACTTGGTTCT GGTCTTGTGA CAACCCCTGA AGGGGAGACC TGCACCATCA AGAAACCAA     5760

GCTCTCTGAC CTTTCCAGAC ATTTTGCAGG CCCAAGCGTT CCTCTTGGGG ACATTAAATT    5820

GAGTCCGGCC ATCATCCCTG ATGTAACATC CATTCCGAGT GACTTGGCAT CGCTCCTAGC    5880

CTCCGTCCCT GTAGTGGAAG GCGGCCTCTC GACCGTTCAA CTTTTGTGTG TCTTTTTCCT    5940

TCTCTGGCGC ATGATGGGCC ATGCCTGGAC ACCCATTGTT GCCGTGGGCT TCTTTTTGCT    6000

GAATGAAATT CTTCCAGCAG TTTTGGTCCG AGCCGTGTTT TCTTTTGCAC TCTTTGTGCT    6060

TGCATGGGCC ACCCCCTGGT CTGCACAGGT GTTGATGATT AGACTCCTCA CGGCATCTCT    6120

CAACCGCAAC AAGCTTTCTC TGGCGTTCTA CGCACTCGGG GGTGTCGTCG GTTTGGCAGC    6180

TGAAATCGGG ACTTTTGCTG GCAGATTGTC TGAATTGTCT CAAGCTCTTT CGACATACTG    6240

CTTCTTACCT AGGGTCCTTG CTATGACCAG TTGTGTTCCC ACCATCATCA TTGGTGGACT    6300

CCATACCCTC GGTGTGATTC TGTGGTTATT CAAATACCGG TGCCTCCACA ACATGCTGGT    6360

TGGTGATGGG AGTTTTTCAA GCGCCTTCTT CCTACGGTAT TTTGCAGAGG GTAATCTCAG    6420

AAAAGGTGTT TCACAGTCCT GTGGCATGAA TAACGAGTCC CTAACGGCTG CTTTAGCTTG    6480

CAAGTTGTCA CAGGCTGACC TTGATTTTTT GTCCAGCTTA ACGAACTTCA AGTGCTTTGT    6540

ATCTGCTTCA AACATGAAAA ATGCTGCCGG CCAGTACATT GAAGCAGCGT ATGCCAAGGC    6600

CCTGCGCCAA GAGTTGGCCT CTCTAGTTCA GATTGACAAA ATGAAAGGAG TTTTGTCCAA    6660

GCTCGAGGCC TTTGCTGAAA CAGCCACCCC GTCCCTTGAC ATAGGTGACG TGATTGTTCT    6720

GCTTGGGCAA CATCCTCACG GATCCATCCT CGATATTAAT GTGGGACTG AAAGGAAAAC     6780

TGTGTCCGTG CAAGAGACCC GGAGCCTAGG CGGCTCCAAA TTCAGTGTTT GTACTGTCGT    6840

GTCCAACACA CCCGTGGACG CCTTGACCGG CATCCCACTC CAGACACCAA CCCCTCTTTT    6900
```

```
TGAGAATGGT CCGCGTCATC GCAGCGAGGA AGACGATCTT AAAGTCGAGA GGATGAAGAA    6960

ACACTGTGTA TCCCTCGGCT TCCACAACAT CAATGGCAAA GTTTACTGCA AAATTTGGGA    7020

CAAGTCTACC GGTGACACCT TTTACACGGA TGATTCCCGG TACACCCAAG ACCATGCTTT    7080

TCAGGACAGG TCAGCCGACT ACAGAGACAG GGACTATGAG GGTGTGCAAA CCACCCCCCA    7140

ACAGGGATTT GATCCAAAGT CTGAAACCCC TGTTGGCACT GTTGTGATCG GCGGTATTAC    7200

GTATAACAGG TATCTGATCA AAGGTAAGGA GGTTCTGGTC CCCAAGCCTG ACAACTGCCT    7260

TGAAGCTGCC AAGCTGTCCC TTGAGCAAGC TCTCGCTGGG ATGGGCCAAA CTTGCGACCT    7320

TACAGCTGCC GAGGTGGAAA AGCTAAAGCG CATCATTAGT CAACTCCAAG GTTTGACCAC    7380

TGAACAGGCT TTAAACTGTT AGCCGCCAGC GGCTTGACCC GCTGTGGCCG CGGCGGCCTA    7440

GTTGTGACTG AAACGGCGGT AAAAATTATA AAATACCACA GCAGAACTTT CACCTTAGGC    7500

CCTTTAGACC TAAAAGTCAC TTCCGAGGTG GAGGTAAAGA AATCAACTGA GCAGGGCCAC    7560

GCTGTTGTGG CAAACTTATG TTCCGGTGTC ATCTTGATGA GACCTCACCC ACCGTCCCTT    7620

GTCGACGTTC TTCTGAAACC CGGACTTGAC ACAATACCCG GCATTCAACC AGGGCATGGG    7680

GCCGGGAATA TGGGCGTGGA CGGTTCTATT TGGGATTTTG AAACCGCACC CACAAAGGCA    7740

GAACTCGAGT TATCCAAGCA AATAATCCAA GCATGTGAAG TTAGGCGCGG GGACGCCCCG    7800

AACCTCCAAC TCCCTTACAA GCTCTATCCT GTTAGGGGGG ATCCTGAGCG GCATAAAGGC    7860

CGCCTTATCA ATACCAGGTT TGGAGATTTA CCTTACAAAA CTCCTCAAGA CACCAAGTCC    7920

GCAATCCACG CGGCTTGTTG CCTGCACCCC AACGGGCCC CCGTGTCTGA TGGTAAATCC    7980

ACACTAGGTA CCACTCTTCA ACATGGTTTC GAGCTTTATG TCCCTACTGT GCCCTATAGT    8040

GTCATGGAGT ACCTTGATTC ACGCCCTGAC ACCCCTTTTA TGTGTACTAA ACATGGCACT    8100

TCCAAGGCTG CTGCAGAGGA CCTCCAAAAA TACGACCTAT CCACCCAAGG ATTTGTCCTG    8160

CCTGGGGTCC TACGCCTAGT ACGCAGATTC ATCTTTGGCC ATATTGGTAA GGCGCCGCCA    8220

TTGTTCCTCC CATCAACCTA TCCCGCCAAG AACTCTATGG CAGGGATCAA TGGCCAGAGG    8280

TTCCCAACAA AGGACGTTCA GAGCATACCT GAAATTGATG AAATGTGTGC CCGCGCTGTC    8340

AAGGAGAATT GGCAAACTGT GACACCTTGC ACCCTCAAGA AACAGTACTG TTCCAAGCCC    8400

AAAACCAGGA CCATCCTGGG CACCAACAAC TTTATTGCCT TGGCTCACAG ATCGGCGCTC    8460

AGTGGTGTCA CCCAGGCATT CATGAAGAAG GCTTGGAAGT CCCCAATTGC CTTGGGGAAA    8520

AACAAATTCA AGGAGCTGCA TTGCACTGTC GCCGGCAGGT GTCTTGAGGC CGACTTGGCC    8580

TCCTGTGACC GCAGCACCCC CGCCATTGTA AGATGGTTTG TTGCCAACCT CCTGTATGAA    8640

CTTGCAGGAT GTGAAGAGTA CTTGCCTAGC TATGTGCTTA ATTGCTGCCA TGACCTCGTG    8700

GCAACACAGG ATGGTGCCTT CACAAAACGC GGTGGCCTGT CGTCCGGGGA CCCCGTCACC    8760

AGTGTGTCCA ACACCGTATA TTCACTGGTA ATTTATGCCC AGCACATGGT ATTGTCGGCC    8820

TTGAAAATGG GTCATGAAAT TGGTCTTAAG TTCCTCGAGG AACAGCTCAA GTTCGAGGAC    8880

CTCCTTGAAA TTCAGCCTAT GTTGGTATAC TCTGATGATC TTGTCTTGTA CGCTGAAAGA    8940

CCCACATTTC CCAATTACCA CTGGTGGGTC GAGCACCTTG ACCTGATGCT GGGTTTCAGA    9000

ACGGACCCAA AGAAAACCGT CATAACTGAT AAACCCAGCT TCCTCGGCTG CAGAATTGAG    9060

GCAGGGCGAC AGCTAGTCCC CAATCGCGAC CGCATCCTGG CTGCTCTTGC ATATCACATG    9120

AAGGCGCAGA ACGCCTCAGA GTATTATGCG TCTGCTGCCG CAATCCTGAT GGATTCATGT    9180

GCTTGCATTG ACCATGACCC TGAGTGGTAT GAGGACCTCA TCTGCGGTAT TGCCCGGTGC    9240

GCCCGCCAGG ATGGTTATAG CTTCCCAGGT CCGGCATTTT TCATGTCCAT GTGGGAGAAG    9300
```

```
CTGAGAAGTC ATAATGAAGG GAAGAAATTC CGCCACTGCG GCATCTGCGA CGCCAAAGCC    9360

GACTATGCGT CCGCCTGTGG GCTTGATTTG TGTTTGTTCC ATTCGCACTT TCATCAACAC    9420

TGCCCTGTCA CTCTGAGCTG CGGTCACCAT GCCGGTTCAA AGGAATGTTC GCAGTGTCAG    9480

TCACCTGTTG GGGCTGGCAG ATCCCCTCTT GATGCCGTGC TAAAACAAAT TCCATACAAA    9540

CCTCCTCGTA CTGTCATCAT GAAGGTGGGT AATAAAACAA CGGCCCTCGA TCCGGGGAGG    9600

TACCAGTCCC GTCGAGGTCT CGTTGCAGTC AAGAGGGGTA TTGCAGGCAA TGAAGTTGAT    9660

CTTTCTGATG GGGACTACCA AGTGGTGCCT CTTTTGCCGA CTTGCAAAGA CATAAACATG    9720

GTGAAGGTGG CTTGCAATGT ACTACTCAGC AAGTTCATAG TAGGGCCACC AGGTTCCGGA    9780

AAGACCACCT GGCTACTGAG TCAAGTCCAG GACGATGATG TCATTTACAC ACCCACCCAT    9840

CAGACTATGT TTGATATAGT CAGTGCTCTC AAAGTTTGCA GGTATTCCAT TCCAGGAGCC    9900

TCAGGACTCC CTTTCCCACC ACCTGCCAGG TCCGGGCCGT GGGTTAGGCT TATTGCCAGC    9960

GGGCACGTCC CTGGCCGAGT ATCATACCTC GATGAGGCTG GATATTGTAA TCATCTGGAC   10020

ATTCTTAGAC TGCTTTCCAA AACACCCCTT GTGTGTTTGG GTGACCTTCA GCAACTTCAC   10080

CCTGTCGGCT TTGATTCCTA CTGTTATGTG TTCGATCAGA TGCCTCAGAA GCAGCTGACC   10140

ACTATTTACA GATTTGGCCC TAACATCTGC GCACGCATCC AGCCTTGTTA CAGGGAGAAA   10200

CTTGAATCTA AGGCTAGGAA CACTAGGGTG GTTTTTACCA CCCGGCCTGT GGCCTTTGGT   10260

CAGGTGCTGA CACCATACCA TAAAGATCGC ATCGGCTCTG CGATAACCAT AGATTCATCC   10320

CAGGGGGCCA CCTTTGATAT TGTGACATTG CATCTACCAT CGCCAAAGTC CCTAAATAAA   10380

TCCCGAGCAC TTGTAGCCAT CACTCGGGCA AGACACGGGT TGTTCATTTA TGACCCTCAT   10440

AACCAGCTCC AGGAGTTTTT CAACTTAACC CCTGAGCGCA CTGATTGTAA CCTTGTGTTC   10500

AGCCGTGGGG ATGAGCTGGT AGTTCTGAAT GCGGATAATG CAGTCACAAC TGTAGCGAAG   10560

GCCCTTGAGA CAGGTCCATC TCGATTTCGA GTATCAGACC CGAGGTGCAA GTCTCTCTTA   10620

GCCGCTTGTT CGGCCAGTCT GGAAGGGAGC TGTATGCCAC TACCGCAAGT GGCACATAAC   10680

CTGGGGTTTT ACTTTTCCCC GGACAGTCCA ACATTTGCAC CTCTGCCAAA AGAGTTGGCG   10740

CCACATTGGC CAGTGGTTAC CCACCAGAAT AATCGGGCGT GGCCTGATCG ACTTGTCGCT   10800

AGTATGCGCC CAATTGATGC CCGCTACAGC AAGCCAATGG TCGGTGCAGG GTATGTGGTC   10860

GGGCCGTCCA CCTTTCTTGG TACTCCTGGT GTGGTGTCAT ACTATCTCAC ACTATACATC   10920

AGGGGTGAGC CCCAGGCCTT GCCAGAAACA CTCGTTTCAA CAGGGCGTAT AGCCACAGAT   10980

TGTCGGGAGT ATCTCGACGC GGCTGAGGAA GAGGCAGCAA AGAACTCCC  CCACGCATTC   11040

ATTGGCGATG TCAAAGGTAC CACGGTTGGG GGGTGTCATC ACATTACATC AAAATACCTA   11100

CCTAGGTCCC TGCCTAAGGA CTCTGTTGCC GTAGTTGGAG TAAGTTCGCC CGGCAGGGCT   11160

GCTAAAGCCG TGTGCACTCT CACCGATGTG TACCTCCCCG AACTCCGGCC ATATCTGCAA   11220

CCTGAGACGG CATCAAAATG CTGGAAACTC AAATTAGACT TCAGGGACGT CCGACTAATG   11280

GTCTGGAAAG GAGCCACCGC CTATTTCCAG TTGGAAGGGC TTACATGGTC GGCGCTGCCC   11340

GACTATGCCA GGTTTATTCA GCTGCCCAAG GATGCCGTTG TATACATTGA TCCGTGTATA   11400

GGACCGGCAA CAGCCAACCG TAAGGTCGTG CGAACCACAG ACTGGCGGGC CGACCTGGCA   11460

GTGACACCGT ATGATTACGG TGCCCAGAAC ATTTTGACAA CAGCCTGGTT CGAGGACCTC   11520

GGGCCGCAGT GGAAGATTTT GGGGTTGCAG CCCTTTAGGC GAGCATTTGG CTTTGAAAAC   11580

ACTGAGGATT GGGCAATCCT TGCACGCCGT ATGAATGACG GCAAGGACTA CACTGACTAT   11640

AACTGGAACT GTGTTCGAGA ACGCCCACAC GCCATCTACG GGCGTGCTCG TGACCATACG   11700
```

-continued

```
TATCATTTTG CCCCTGGCAC AGAATTGCAG GTAGAGCTAG GTAAACCCCG GCTGCCGCCT   11760
GGGCAAGTGC CGTGAATTCG GGGTGATGCA ATGGGGTCAC TGTGGAGTAA AATCAGCCAG   11820
CTGTTCGTGG ACGCCTTCAC TGAGTTCCTT GTTAGTGTGG TTGATATTGC CATTTTCCTT   11880
GCCATACTGT TTGGGTTCAC CGTCGCAGGA TGGTTACTGG TCTTTCTTCT CAGAGTGGTT   11940
TGCTCCGCGC TTCTCCGTTC GCGCTCTGCC ATTCACTCTC CCGAACTATC GAAGGTCCTA   12000
TGAAGGCTTG TTGCCCAACT GCAGACCGGA TGTCCCACAA TTTGCAGTCA AGCACCCATT   12060
GGGTATGTTT TGGCACATGC GAGTTTCCCA CTTGATTGAT GAGATGGTCT CTCGTCGCAT   12120
TTACCAGACC ATGGAACATT CAGGTCAAGC GGCCTGGAAG CAGGTGGTTG GTGAGGCCAC   12180
TCTCACGAAG CTGTCAGGGC TCGATATAGT TACTCATTTC CAACACCTGG CCGCAGTGGA   12240
GGCGGATTCT TGCCGCTTTC TCAGCTCACG ACTCGTGATG CTAAAAAATC TTGCCGTTGG   12300
CAATGTGAGC CTACAGTACA ACACCACGTT GGACCGCGTT GAGCTCATCT TCCCCACGCC   12360
AGGTACGAGG CCCAAGTTGA CCGATTTCAG ACAATGGCTC ATCAGTGTGC ACGCTTCCAT   12420
TTTTTCCTCT GTGGCTTCAT CTGTTACCTT GTTCATAGTG CTTTGGCTTC GAATTCCAGC   12480
TCTACGCTAT GTTTTTGGTT TCCATTGGCC CACGGCAACA CATCATTCGA GCTGACCATC   12540
AACTACACCA TATGCATGCC CTGTTCTACC AGTCAAGCGG CTCGCCAAAG GCTCGAGCCC   12600
GGTCGTAACA TGTGGTGCAA AATAGGGCAT GACAGGTGTG AGGAGCGTGA CCATGATGAG   12660
TTGTTAATGT CCATCCCGTC CGGGTACGAC AACCTCAAAC TTGAGGGTTA TTATGCTTGG   12720
CTGGCTTTTT TGTCCTTTTC CTACGCGGCC CAATTCCATC CGGAGTTGTT CGGGATAGGG   12780
AATGTGTCGC GCGTCTTCGT GGACAAGCGA CACCAGTTCA TTTGTGCCGA GCATGATGGA   12840
CACAATTCAA CCGTATCTAC CGGACACAAC ATCTCCGCAT TATATGCGGC ATATTACCAC   12900
CACCAAATAG ACGGGGGCAA TTGGTTCCAT TTGGAATGGC TGCGGCCACT CTTTTCTTCC   12960
TGGCTGGTGC TCAACATATC ATGGTTTCTG AGGCGTTCGC CTGTAAGCCC TGTTTCTCGA   13020
CGCATCTATC AGATATTGAG ACCAACACGA CCGCGGCTGC CGGTTTCATG GTCCTTCAGG   13080
ACATCAATTG TTTCCGACCT CACGGGGTCT CAGCAGCGCA AGAGAAAATT TCCTTCGGAA   13140
AGTCGTCCCA ATGTCGTGAA GCCGTCGGTA CTCCCCAGTA CATCACGATA ACGGCTAACG   13200
TGACCGACGA ATCATACTTG TACAACGCGG ACCTGCTGAT GCTTTCTGCG TGCCTTTTCT   13260
ACGCCTCAGA AATGAGCGAG AAAGGCTTCA AAGTCATCTT TGGGAATGTC TCTGGCGTTG   13320
TTTCTGCTTG TGTCAATTTC ACAGATTATG TGGCCCATGT GACCCAACAT ACCCAGCAGC   13380
ATCATCTGGT AATTGATCAC ATTCGGTTGC TGCATTTCCT GACACCATCT GCAATGAGGT   13440
GGGCTACAAC CATTGCTTGT TTGTTCGCCA TTCTCTTGGC AATATGAGAT GTTCTCACAA   13500
ATTGGGGCGT TTCTTGACTC CGCACTCTTG CTTCTGGTGG CTTTTTTTGC TGTGTACCGG   13560
CTTGTCCTGG TCCTTTGCCG ATGGCAACGG CGACAGCTCG ACATACCAAT ACATATATAA   13620
CTTGACGATA TGCGAGCTGA ATGGGACCGA CTGGTTGTCC AGCCATTTTG GTTGGGCAGT   13680
CGAGACCTTT GTGCTTTACC CGGTTGCCAC TCATATCCTC TCACTGGGTT TTCTCACAAC   13740
AAGCCATTTT TTTGACGCGC TCGGTCTCGG CGCTGTATCC ACTGCAGGAT TGTTGGCGG   13800
GCGGTACGTA CTCTGCAGCG TCTACGGCGC TTGTGCTTTC GCAGCGTTCG TATGTTTTGT   13860
CATCCGTGCT GCTAAAAATT GCATGGCCTG CCGCTATGCC CGTACCCGGT TTACCAACTT   13920
CATTGTGGAC GACCGGGGA GAGTTCATCG ATGGAAGTCT CCAATAGTGG TAGAAAAATT   13980
GGGCAAAGCC GAAGTCGATG GCAACCTCGT CACCATCAAA CATGTCGTCC TCGAAGGGGT   14040
TAAAGCTCAA CCCTTGACGA GGACTTCGGC TGAGCAATGG GAGGCCTAGA CGATTTTTGC   14100
```

```
AACGATCCTA TCGCCGCACA AAAGCTCGTG CTAGCCTTTA GCATCACATA CACACCTATA    14160

ATGATATACG CCCTTAAGGT GTCACGCGGC CGACTCCTGG GGCTGTTGCA CATCCTAATA    14220

TTTCTGAACT GTTCCTTTAC ATTCGGATAC ATGACATATG TGCATTTTCA ATCCACCAAC    14280

CGTGTCGCAC TTACCCTGGG GGCTGTTGTC GCCCTTCTGT GGGGTGTTTA CAGCTTCACA    14340

GAGTCATGGA AGTTTATCAC TTCCAGATGC AGATTGTGTT GCCTTGGCCG GCGATACATT    14400

CTGGCCCCTG CCCATCACGT AGAAAGTGCT GCAGGTCTCC ATTCAATCTC AGCGTCTGGT    14460

AACCGAGCAT ACGCTGTGAG AAAGCCCGGA CTAACATCAG TGAACGGCAC TCTAGTACCA    14520

GGACTTCGGA GCCTCGTGCT GGGCGGCAAA CGAGCTGTTA AACGAGGAGT GGTTAACCTC    14580

GTCAAGTATG GCCGGTAAAA ACCAGAGCCA GAAGAAAAAG AAAAGTACAG CTCCGATGGG    14640

GAATGGCCAG CCAGTCAATC AACTGTGCCA GTTGCTGGGT GCAATGATAA AGTCCCAGCG    14700

CCAGCAACCT AGGGGAGGAC AGGCCAAAAA GAAAAAGCCT GAGAAGCCAC ATTTTCCCCT    14760

GGCTGCTGAA GATGACATCC GGCACCACCT CACCCAGACT GAACGCTCCC TCTGCTTGCA    14820

ATCGATCCAG ACGGCTTTCA ATCAAGGCGC AGGAACTGCG TCGCTTTCAT CCAGCGGGAA    14880

GGTCAGTTTT CAGGTTGAGT TTATGCTGCC GGTTGCTCAT ACAGTGCGCC TGATTCGCGT    14940

GACTTCTACA TCCGCCAGTC AGGGTGCAAG TTAATTTGAC AGTCAGGTGA ATGGCCGCGA    15000

TTGGCGTGTG GCCTCTGAGT CACCTATTCA ATTAGGGCGA TCACATGGGG GTCATACTTA    15060

ATCAGGCAGG AACCATGTGA CCGAAATTAA AAAAAAAAA A                        15101
```

(2) INFORMATION FOR SEQ ID NO:15:

(i) SEQUENCE CHARACTERISTICS:
        (A) LENGTH: 747 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..747
        (D) OTHER INFORMATION: /standard_name= "LV ORF 2"

(xi) SEQUENCE DESCRIPTION: SEQ ID NO:15:

```
ATG CAA TGG GGT CAC TGT GGA GTA AAA TCA GCC AGC TGT TCG TGG ACG         48
Met Gln Trp Gly His Cys Gly Val Lys Ser Ala Ser Cys Ser Trp Thr
 1               5                  10                  15

CCT TCA CTG AGT TCC TTG TTA GTG TGG TTG ATA TTG CCA TTT TCC TTG         96
Pro Ser Leu Ser Ser Leu Leu Val Trp Leu Ile Leu Pro Phe Ser Leu
                20                  25                  30

CCA TAC TGT TTG GGT TCA CCG TCG CAG GAT GGT TAC TGG TCT TTC TTC        144
Pro Tyr Cys Leu Gly Ser Pro Ser Gln Asp Gly Tyr Trp Ser Phe Phe
            35                  40                  45

TCA GAG TGG TTT GCT CCG CGC TTC TCC GTT CGC GCT CTG CCA TTC ACT        192
Ser Glu Trp Phe Ala Pro Arg Phe Ser Val Arg Ala Leu Pro Phe Thr
        50                  55                  60

CTC CCG AAC TAT CGA AGG TCC TAT GAA GGC TTG TTG CCC AAC TGC AGA        240
Leu Pro Asn Tyr Arg Arg Ser Tyr Glu Gly Leu Leu Pro Asn Cys Arg
65                  70                  75                  80

CCG GAT GTC CCA CAA TTT GCA GTC AAG CAC CCA TTG GGT ATG TTT TGG        288
Pro Asp Val Pro Gln Phe Ala Val Lys His Pro Leu Gly Met Phe Trp
                    85                  90                  95

CAC ATG CGA GTT TCC CAC TTG ATT GAT GAG ATG GTC TCT CGT CGC ATT        336
His Met Arg Val Ser His Leu Ile Asp Glu Met Val Ser Arg Arg Ile
                100                 105                 110
```

-continued

```
TAC CAG ACC ATG GAA CAT TCA GGT CAA GCG GCC TGG AAG CAG GTG GTT       384
Tyr Gln Thr Met Glu His Ser Gly Gln Ala Ala Trp Lys Gln Val Val
            115                 120                 125

GGT GAG GCC ACT CTC ACG AAG CTG TCA GGG CTC GAT ATA GTT ACT CAT       432
Gly Glu Ala Thr Leu Thr Lys Leu Ser Gly Leu Asp Ile Val Thr His
130                 135                 140

TTC CAA CAC CTG GCC GCA GTG GAG GCG GAT TCT TGC CGC TTT CTC AGC       480
Phe Gln His Leu Ala Ala Val Glu Ala Asp Ser Cys Arg Phe Leu Ser
145                 150                 155                 160

TCA CGA CTC GTG ATG CTA AAA AAT CTT GCC GTT GGC AAT GTG AGC CTA       528
Ser Arg Leu Val Met Leu Lys Asn Leu Ala Val Gly Asn Val Ser Leu
            165                 170                 175

CAG TAC AAC ACC ACG TTG GAC CGC GTT GAG CTC ATC TTC CCC ACG CCA       576
Gln Tyr Asn Thr Thr Leu Asp Arg Val Glu Leu Ile Phe Pro Thr Pro
            180                 185                 190

GGT ACG AGG CCC AAG TTG ACC GAT TTC AGA CAA TGG CTC ATC AGT GTG       624
Gly Thr Arg Pro Lys Leu Thr Asp Phe Arg Gln Trp Leu Ile Ser Val
            195                 200                 205

CAC GCT TCC ATT TTT TCC TCT GTG GCT TCA TCT GTT ACC TTG TTC ATA       672
His Ala Ser Ile Phe Ser Ser Val Ala Ser Ser Val Thr Leu Phe Ile
210                 215                 220

GTG CTT TGG CTT CGA ATT CCA GCT CTA CGC TAT GTT TTT GGT TTC CAT       720
Val Leu Trp Leu Arg Ile Pro Ala Leu Arg Tyr Val Phe Gly Phe His
225                 230                 235                 240

TGG CCC ACG GCA ACA CAT CAT TCG AGC                                   747
Trp Pro Thr Ala Thr His His Ser Ser
                245
```

(2) INFORMATION FOR SEQ ID NO:16:

(i) SEQUENCE CHARACTERISTICS:
        (A) LENGTH: 249 amino acids
        (B) TYPE: amino acid
        (D) TOPOLOGY: linear (ii) MOLECULE TYPE: protein (xi) SEQUENCE DESCRIPTION: SEQ ID NO:16:

```
Met Gln Trp Gly His Cys Gly Val Lys Ser Ala Ser Cys Ser Trp Thr
1               5                   10                  15

Pro Ser Leu Ser Ser Leu Leu Val Trp Leu Ile Leu Pro Phe Ser Leu
            20                  25                  30

Pro Tyr Cys Leu Gly Ser Pro Ser Gln Asp Gly Tyr Trp Ser Phe Phe
        35                  40                  45

Ser Glu Trp Phe Ala Pro Arg Phe Ser Val Arg Ala Leu Pro Phe Thr
50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Val Lys His Pro Leu Gly Met Phe Trp
                85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
        115                 120                 125

Gly Glu Ala Thr Leu Thr Lys Leu Ser Gly Leu Asp Ile Val Thr His
130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
            165                 170                 175
```

```
Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
            195                 200                 205

His Ala Ser Ile Phe Ser Ser Val Ala Ser Ser Val Thr Leu Phe Ile
            210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245
```

(2) INFORMATION FOR SEQ ID NO:17:

(i) SEQUENCE CHARACTERISTICS:
        (A) LENGTH: 795 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..795
        (D) OTHER INFORMATION: /standard_name= "LV ORF 3"

(xi) SEQUENCE DESCRIPTION: SEQ ID NO:17:

```
ATG GCT CAT CAG TGT GCA CGC TTC CAT TTT TTC CTC TGT GGC TTC ATC        48
Met Ala His Gln Cys Ala Arg Phe His Phe Phe Leu Cys Gly Phe Ile
 1               5                  10                  15

TGT TAC CTT GTT CAT AGT GCT TTG GCT TCG AAT TCC AGC TCT ACG CTA        96
Cys Tyr Leu Val His Ser Ala Leu Ala Ser Asn Ser Ser Ser Thr Leu
             20                  25                  30

TGT TTT TGG TTT CCA TTG GCC CAC GGC AAC ACA TCA TTC GAG CTG ACC       144
Cys Phe Trp Phe Pro Leu Ala His Gly Asn Thr Ser Phe Glu Leu Thr
         35                  40                  45

ATC AAC TAC ACC ATA TGC ATG CCC TGT TCT ACC AGT CAA GCG GCT CGC       192
Ile Asn Tyr Thr Ile Cys Met Pro Cys Ser Thr Ser Gln Ala Ala Arg
     50                  55                  60

CAA AGG CTC GAG CCC GGT CGT AAC ATG TGG TGC AAA ATA GGG CAT GAC       240
Gln Arg Leu Glu Pro Gly Arg Asn Met Trp Cys Lys Ile Gly His Asp
 65                  70                  75                  80

AGG TGT GAG GAG CGT GAC CAT GAT GAG TTG TTA ATG TCC ATC CCG TCC       288
Arg Cys Glu Glu Arg Asp His Asp Glu Leu Leu Met Ser Ile Pro Ser
                 85                  90                  95

GGG TAC GAC AAC CTC AAA CTT GAG GGT TAT TAT GCT TGG CTG GCT TTT       336
Gly Tyr Asp Asn Leu Lys Leu Glu Gly Tyr Tyr Ala Trp Leu Ala Phe
            100                 105                 110

TTG TCC TTT TCC TAC GCG GCC CAA TTC CAT CCG GAG TTG TTC GGG ATA       384
Leu Ser Phe Ser Tyr Ala Ala Gln Phe His Pro Glu Leu Phe Gly Ile
        115                 120                 125

GGG AAT GTG TCG CGC GTC TTC GTG GAC AAG CGA CAC CAG TTC ATT TGT       432
Gly Asn Val Ser Arg Val Phe Val Asp Lys Arg His Gln Phe Ile Cys
    130                 135                 140

GCC GAG CAT GAT GGA CAC AAT TCA ACC GTA TCT ACC GGA CAC AAC ATC       480
Ala Glu His Asp Gly His Asn Ser Thr Val Ser Thr Gly His Asn Ile
145                 150                 155                 160

TCC GCA TTA TAT GCG GCA TAT TAC CAC CAC CAA ATA GAC GGG GGC AAT       528
Ser Ala Leu Tyr Ala Ala Tyr Tyr His His Gln Ile Asp Gly Gly Asn
                165                 170                 175

TGG TTC CAT TTG GAA TGG CTG CGG CCA CTC TTT TCT TCC TGG CTG GTG       576
Trp Phe His Leu Glu Trp Leu Arg Pro Leu Phe Ser Ser Trp Leu Val
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     |     | 180 |     |     |     | 185 |     |     |     | 190 |     |     |     |     |
| CTC | AAC | ATA | TCA | TGG | TTT | CTG | AGG | CGT | TCG | CCT | GTA | AGC | CCT | GTT | TCT | 624 |
| Leu | Asn | Ile | Ser | Trp | Phe | Leu | Arg | Arg | Ser | Pro | Val | Ser | Pro | Val | Ser |     |
|     |     | 195 |     |     |     | 200 |     |     |     | 205 |     |     |     |     |     |     |
| CGA | CGC | ATC | TAT | CAG | ATA | TTG | AGA | CCA | ACA | CGA | CCG | CGG | CTG | CCG | GTT | 672 |
| Arg | Arg | Ile | Tyr | Gln | Ile | Leu | Arg | Pro | Thr | Arg | Pro | Arg | Leu | Pro | Val |     |
|     | 210 |     |     |     |     | 215 |     |     |     |     | 220 |     |     |     |     |     |
| TCA | TGG | TCC | TTC | AGG | ACA | TCA | ATT | GTT | TCC | GAC | CTC | ACG | GGG | TCT | CAG | 720 |
| Ser | Trp | Ser | Phe | Arg | Thr | Ser | Ile | Val | Ser | Asp | Leu | Thr | Gly | Ser | Gln |     |
| 225 |     |     |     |     | 230 |     |     |     |     | 235 |     |     |     |     | 240 |     |
| CAG | CGC | AAG | AGA | AAA | TTT | CCT | TCG | GAA | AGT | CGT | CCC | AAT | GTC | GTG | AAG | 768 |
| Gln | Arg | Lys | Arg | Lys | Phe | Pro | Ser | Glu | Ser | Arg | Pro | Asn | Val | Val | Lys |     |
|     |     |     |     | 245 |     |     |     | 250 |     |     |     | 255 |     |     |     |     |
| CCG | TCG | GTA | CTC | CCC | AGT | ACA | TCA | CGA |     |     |     |     |     |     |     | 795 |
| Pro | Ser | Val | Leu | Pro | Ser | Thr | Ser | Arg |     |     |     |     |     |     |     |     |
|     |     |     | 260 |     |     |     | 265 |     |     |     |     |     |     |     |     |     |

(2) INFORMATION FOR SEQ ID NO:18:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO:18:

```
Met Ala His Gln Cys Ala Arg Phe His Phe Phe Leu Cys Gly Phe Ile
  1               5                  10                  15

Cys Tyr Leu Val His Ser Ala Leu Ala Ser Asn Ser Ser Ser Thr Leu
             20                  25                  30

Cys Phe Trp Phe Pro Leu Ala His Gly Asn Thr Ser Phe Glu Leu Thr
         35                  40                  45

Ile Asn Tyr Thr Ile Cys Met Pro Cys Ser Thr Ser Gln Ala Ala Arg
     50                  55                  60

Gln Arg Leu Glu Pro Gly Arg Asn Met Trp Cys Lys Ile Gly His Asp
 65                  70                  75                  80

Arg Cys Glu Glu Arg Asp His Asp Glu Leu Leu Met Ser Ile Pro Ser
                 85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
        115                 120                 125

Gly Asn Val Ser Arg Val Phe Val Asp Lys Arg His Gln Phe Ile Cys
    130                 135                 140

Ala Glu His Asp Gly His Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Arg Leu Pro Val
    210                 215                 220

Ser Trp Ser Phe Arg Thr Ser Ile Val Ser Asp Leu Thr Gly Ser Gln
225                 230                 235                 240

Gln Arg Lys Arg Lys Phe Pro Ser Glu Ser Arg Pro Asn Val Val Lys
```

```
                    245                 250                 255
Pro Ser Val Leu Pro Ser Thr Ser Arg
            260                 265

(2) INFORMATION FOR SEQ ID NO:19:

(i) SEQUENCE CHARACTERISTICS:
        (A) LENGTH: 549 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..549
        (D) OTHER INFORMATION: /standard_name= "LV ORF 4"

(xi) SEQUENCE DESCRIPTION: SEQ ID NO:19:

ATG GCT GCG GCC ACT CTT TTC TTC CTG GCT GGT GCT CAA CAT ATC ATG      48
Met Ala Ala Ala Thr Leu Phe Phe Leu Ala Gly Ala Gln His Ile Met
  1               5                  10                  15

GTT TCT GAG GCG TTC GCC TGT AAG CCC TGT TTC TCG ACG CAT CTA TCA      96
Val Ser Glu Ala Phe Ala Cys Lys Pro Cys Phe Ser Thr His Leu Ser
                 20                  25                  30

GAT ATT GAG ACC AAC ACG ACC GCG GCT GCC GGT TTC ATG GTC CTT CAG     144
Asp Ile Glu Thr Asn Thr Thr Ala Ala Ala Gly Phe Met Val Leu Gln
         35                  40                  45

GAC ATC AAT TGT TTC CGA CCT CAC GGG GTC TCA GCA GCG CAA GAG AAA     192
Asp Ile Asn Cys Phe Arg Pro His Gly Val Ser Ala Ala Gln Glu Lys
 50                  55                  60

ATT TCC TTC GGA AAG TCG TCC CAA TGT CGT GAA GCC GTC GGT ACT CCC     240
Ile Ser Phe Gly Lys Ser Ser Gln Cys Arg Glu Ala Val Gly Thr Pro
 65                  70                  75                  80

CAG TAC ATC ACG ATA ACG GCT AAC GTG ACC GAC GAA TCA TAC TTG TAC     288
Gln Tyr Ile Thr Ile Thr Ala Asn Val Thr Asp Glu Ser Tyr Leu Tyr
                 85                  90                  95

AAC GCG GAC CTG CTG ATG CTT TCT GCG TGC CTT TTC TAC GCC TCA GAA     336
Asn Ala Asp Leu Leu Met Leu Ser Ala Cys Leu Phe Tyr Ala Ser Glu
            100                 105                 110

ATG AGC GAG AAA GGC TTC AAA GTC ATC TTT GGG AAT GTC TCT GGC GTT     384
Met Ser Glu Lys Gly Phe Lys Val Ile Phe Gly Asn Val Ser Gly Val
        115                 120                 125

GTT TCT GCT TGT GTC AAT TTC ACA GAT TAT GTG GCC CAT GTG ACC CAA     432
Val Ser Ala Cys Val Asn Phe Thr Asp Tyr Val Ala His Val Thr Gln
    130                 135                 140

CAT ACC CAG CAG CAT CAT CTG GTA ATT GAT CAC ATT CGG TTG CTG CAT     480
His Thr Gln Gln His His Leu Val Ile Asp His Ile Arg Leu Leu His
145                 150                 155                 160

TTC CTG ACA CCA TCT GCA ATG AGG TGG GCT ACA ACC ATT GCT TGT TTG     528
Phe Leu Thr Pro Ser Ala Met Arg Trp Ala Thr Thr Ile Ala Cys Leu
                165                 170                 175

TTC GCC ATT CTC TTG GCA ATA                                         549
Phe Ala Ile Leu Leu Ala Ile
                180

(2) INFORMATION FOR SEQ ID NO:20:

(i) SEQUENCE CHARACTERISTICS:
        (A) LENGTH: 183 amino acids
        (B) TYPE: amino acid
        (D) TOPOLOGY: linear (ii) MOLECULE TYPE: protein
```

(xi) SEQUENCE DESCRIPTION: SEQ ID NO:20:

```
Met Ala Ala Ala Thr Leu Phe Phe Leu Ala Gly Ala Gln His Ile Met
  1               5                  10                  15

Val Ser Glu Ala Phe Ala Cys Lys Pro Cys Phe Ser Thr His Leu Ser
             20                  25                  30

Asp Ile Glu Thr Asn Thr Thr Ala Ala Ala Gly Phe Met Val Leu Gln
         35                  40                  45

Asp Ile Asn Cys Phe Arg Pro His Gly Val Ser Ala Gln Glu Lys
     50                  55                  60

Ile Ser Phe Gly Lys Ser Ser Gln Cys Arg Glu Ala Val Gly Thr Pro
 65                  70                  75                  80

Gln Tyr Ile Thr Ile Thr Ala Asn Val Thr Asp Glu Ser Tyr Leu Tyr
                 85                  90                  95

Asn Ala Asp Leu Leu Met Leu Ser Ala Cys Leu Phe Tyr Ala Ser Glu
                100                 105                 110

Met Ser Glu Lys Gly Phe Lys Val Ile Phe Gly Asn Val Ser Gly Val
            115                 120                 125

Val Ser Ala Cys Val Asn Phe Thr Asp Tyr Val Ala His Val Thr Gln
        130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
                180
```

(2) INFORMATION FOR SEQ ID NO:21:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..603
        (D) OTHER INFORMATION: /standard_name= "LV ORF 5"

(xi) SEQUENCE DESCRIPTION: SEQ ID NO:21:

```
ATG AGA TGT TCT CAC AAA TTG GGG CGT TTC TTG ACT CCG CAC TCT TGC     48
Met Arg Cys Ser His Lys Leu Gly Arg Phe Leu Thr Pro His Ser Cys
  1               5                  10                  15

TTC TGG TGG CTT TTT TTG CTG TGT ACC GGC TTG TCC TGG TCC TTT GCC     96
Phe Trp Trp Leu Phe Leu Leu Cys Thr Gly Leu Ser Trp Ser Phe Ala
             20                  25                  30

GAT GGC AAC GGC GAC AGC TCG ACA TAC CAA TAC ATA TAT AAC TTG ACG    144
Asp Gly Asn Gly Asp Ser Ser Thr Tyr Gln Tyr Ile Tyr Asn Leu Thr
         35                  40                  45

ATA TGC GAG CTG AAT GGG ACC GAC TGG TTG TCC AGC CAT TTT GGT TGG    192
Ile Cys Glu Leu Asn Gly Thr Asp Trp Leu Ser Ser His Phe Gly Trp
     50                  55                  60

GCA GTC GAG ACC TTT GTG CTT TAC CCG GTT GCC ACT CAT ATC CTC TCA    240
Ala Val Glu Thr Phe Val Leu Tyr Pro Val Ala Thr His Ile Leu Ser
 65                  70                  75                  80

CTG GGT TTT CTC ACA ACA AGC CAT TTT TTT GAC GCG CTC GGT CTC GGC    288
Leu Gly Phe Leu Thr Thr Ser His Phe Phe Asp Ala Leu Gly Leu Gly
                 85                  90                  95
```

```
GCT GTA TCC ACT GCA GGA TTT GTT GGC GGG CGG TAC GTA CTC TGC AGC      336
Ala Val Ser Thr Ala Gly Phe Val Gly Gly Arg Tyr Val Leu Cys Ser
        100                 105                 110

GTC TAC GGC GCT TGT GCT TTC GCA GCG TTC GTA TGT TTT GTC ATC CGT      384
Val Tyr Gly Ala Cys Ala Phe Ala Ala Phe Val Cys Phe Val Ile Arg
            115                 120                 125

GCT GCT AAA AAT TGC ATG GCC TGC CGC TAT GCC CGT ACC CGG TTT ACC      432
Ala Ala Lys Asn Cys Met Ala Cys Arg Tyr Ala Arg Thr Arg Phe Thr
    130                 135                 140

AAC TTC ATT GTG GAC GAC CGG GGG AGA GTT CAT CGA TGG AAG TCT CCA      480
Asn Phe Ile Val Asp Asp Arg Gly Arg Val His Arg Trp Lys Ser Pro
145                 150                 155                 160

ATA GTG GTA GAA AAA TTG GGC AAA GCC GAA GTC GAT GGC AAC CTC GTC      528
Ile Val Val Glu Lys Leu Gly Lys Ala Glu Val Asp Gly Asn Leu Val
                165                 170                 175

ACC ATC AAA CAT GTC GTC CTC GAA GGG GTT AAA GCT CAA CCC TTG ACG      576
Thr Ile Lys His Val Val Leu Glu Gly Val Lys Ala Gln Pro Leu Thr
            180                 185                 190

AGG ACT TCG GCT GAG CAA TGG GAG GCC                                   603
Arg Thr Ser Ala Glu Gln Trp Glu Ala
        195                 200

(2) INFORMATION FOR SEQ ID NO:22:

(i) SEQUENCE CHARACTERISTICS:
        (A) LENGTH: 201 amino acids
        (B) TYPE: amino acid
        (D) TOPOLOGY: linear (ii) MOLECULE TYPE: protein (xi) SEQUENCE DESCRIPTION: SEQ ID NO:22:

Met Arg Cys Ser His Lys Leu Gly Arg Phe Leu Thr Pro His Ser Cys
 1               5                  10                  15

Phe Trp Trp Leu Phe Leu Leu Cys Thr Gly Leu Ser Trp Ser Phe Ala
                20                  25                  30

Asp Gly Asn Gly Asp Ser Ser Thr Tyr Gln Tyr Ile Tyr Asn Leu Thr
            35                  40                  45

Ile Cys Glu Leu Asn Gly Thr Asp Trp Leu Ser Ser His Phe Gly Trp
    50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
    130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200
```

(2) INFORMATION FOR SEQ ID NO:23:

(i) SEQUENCE CHARACTERISTICS:
        (A) LENGTH: 519 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..519
        (D) OTHER INFORMATION: /standard_name= "LV ORF 6"

(xi) SEQUENCE DESCRIPTION: SEQ ID NO:23:

```
ATG GGA GGC CTA GAC GAT TTT TGC AAC GAT CCT ATC GCC GCA CAA AAG        48
Met Gly Gly Leu Asp Asp Phe Cys Asn Asp Pro Ile Ala Ala Gln Lys
 1               5                  10                  15

CTC GTG CTA GCC TTT AGC ATC ACA TAC ACA CCT ATA ATG ATA TAC GCC        96
Leu Val Leu Ala Phe Ser Ile Thr Tyr Thr Pro Ile Met Ile Tyr Ala
             20                  25                  30

CTT AAG GTG TCA CGC GGC CGA CTC CTG GGG CTG TTG CAC ATC CTA ATA       144
Leu Lys Val Ser Arg Gly Arg Leu Leu Gly Leu Leu His Ile Leu Ile
         35                  40                  45

TTT CTG AAC TGT TCC TTT ACA TTC GGA TAC ATG ACA TAT GTG CAT TTT       192
Phe Leu Asn Cys Ser Phe Thr Phe Gly Tyr Met Thr Tyr Val His Phe
     50                  55                  60

CAA TCC ACC AAC CGT GTC GCA CTT ACC CTG GGG GCT GTT GTC GCC CTT       240
Gln Ser Thr Asn Arg Val Ala Leu Thr Leu Gly Ala Val Val Ala Leu
 65                  70                  75                  80

CTG TGG GGT GTT TAC AGC TTC ACA GAG TCA TGG AAG TTT ATC ACT TCC       288
Leu Trp Gly Val Tyr Ser Phe Thr Glu Ser Trp Lys Phe Ile Thr Ser
                 85                  90                  95

AGA TGC AGA TTG TGT TGC CTT GGC CGG CGA TAC ATT CTG GCC CCT GCC       336
Arg Cys Arg Leu Cys Cys Leu Gly Arg Arg Tyr Ile Leu Ala Pro Ala
            100                 105                 110

CAT CAC GTA GAA AGT GCT GCA GGT CTC CAT TCA ATC TCA GCG TCT GGT       384
His His Val Glu Ser Ala Ala Gly Leu His Ser Ile Ser Ala Ser Gly
        115                 120                 125

AAC CGA GCA TAC GCT GTG AGA AAG CCC GGA CTA ACA TCA GTG AAC GGC       432
Asn Arg Ala Tyr Ala Val Arg Lys Pro Gly Leu Thr Ser Val Asn Gly
    130                 135                 140

ACT CTA GTA CCA GGA CTT CGG AGC CTC GTG CTG GGC GGC AAA CGA GCT       480
Thr Leu Val Pro Gly Leu Arg Ser Leu Val Leu Gly Gly Lys Arg Ala
145                 150                 155                 160

GTT AAA CGA GGA GTG GTT AAC CTC GTC AAG TAT GGC CGG                   519
Val Lys Arg Gly Val Val Asn Leu Val Lys Tyr Gly Arg
                165                 170
```

(2) INFORMATION FOR SEQ ID NO:24:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO:24:

```
Met Gly Gly Leu Asp Asp Phe Cys Asn Asp Pro Ile Ala Ala Gln Lys
 1               5                  10                  15

Leu Val Leu Ala Phe Ser Ile Thr Tyr Thr Pro Ile Met Ile Tyr Ala
             20                  25                  30
```

```
Leu Lys Val Ser Arg Gly Arg Leu Leu Gly Leu Leu His Ile Leu Ile
        35                  40                  45

Phe Leu Asn Cys Ser Phe Thr Phe Gly Tyr Met Thr Tyr Val His Phe
 50                  55                  60

Gln Ser Thr Asn Arg Val Ala Leu Thr Leu Gly Ala Val Val Ala Leu
 65                  70                  75                  80

Leu Trp Gly Val Tyr Ser Phe Thr Glu Ser Trp Lys Phe Ile Thr Ser
                 85                  90                  95

Arg Cys Arg Leu Cys Cys Leu Gly Arg Arg Tyr Ile Leu Ala Pro Ala
                100                 105                 110

His His Val Glu Ser Ala Ala Gly Leu His Ser Ile Ser Ala Ser Gly
            115                 120                 125

Asn Arg Ala Tyr Ala Val Arg Lys Pro Gly Leu Thr Ser Val Asn Gly
        130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170
```

(2) INFORMATION FOR SEQ ID NO:25:

(i) SEQUENCE CHARACTERISTICS:
        (A) LENGTH: 384 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..384
        (D) OTHER INFORMATION: /standard_name= "LV ORF 7"

(xi) SEQUENCE DESCRIPTION: SEQ ID NO:25:

```
ATG GCC GGT AAA AAC CAG AGC CAG AAG AAA AAG AAA AGT ACA GCT CCG      48
Met Ala Gly Lys Asn Gln Ser Gln Lys Lys Lys Lys Ser Thr Ala Pro
 1               5                  10                  15

ATG GGG AAT GGC CAG CCA GTC AAT CAA CTG TGC CAG TTG CTG GGT GCA      96
Met Gly Asn Gly Gln Pro Val Asn Gln Leu Cys Gln Leu Leu Gly Ala
             20                  25                  30

ATG ATA AAG TCC CAG CGC CAG CAA CCT AGG GGA GGA CAG GCC AAA AAG     144
Met Ile Lys Ser Gln Arg Gln Gln Pro Arg Gly Gly Gln Ala Lys Lys
         35                  40                  45

AAA AAG CCT GAG AAG CCA CAT TTT CCC CTG GCT GCT GAA GAT GAC ATC     192
Lys Lys Pro Glu Lys Pro His Phe Pro Leu Ala Ala Glu Asp Asp Ile
     50                  55                  60

CGG CAC CAC CTC ACC CAG ACT GAA CGC TCC CTC TGC TTG CAA TCG ATC     240
Arg His His Leu Thr Gln Thr Glu Arg Ser Leu Cys Leu Gln Ser Ile
 65                  70                  75                  80

CAG ACG GCT TTC AAT CAA GGC GCA GGA ACT GCG TCG CTT TCA TCC AGC     288
Gln Thr Ala Phe Asn Gln Gly Ala Gly Thr Ala Ser Leu Ser Ser Ser
                 85                  90                  95

GGG AAG GTC AGT TTT CAG GTT GAG TTT ATG CTG CCG GTT GCT CAT ACA     336
Gly Lys Val Ser Phe Gln Val Glu Phe Met Leu Pro Val Ala His Thr
            100                 105                 110

GTG CGC CTG ATT CGC GTG ACT TCT ACA TCC GCC AGT CAG GGT GCA AGT     384
Val Arg Leu Ile Arg Val Thr Ser Thr Ser Ala Ser Gln Gly Ala Ser
        115                 120                 125
```

(2) INFORMATION FOR SEQ ID NO:26:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:26:

Met Ala Gly Lys Asn Gln Ser Gln Lys Lys Lys Ser Thr Ala Pro
 1               5                  10                  15

Met Gly Asn Gly Gln Pro Val Asn Gln Leu Cys Gln Leu Leu Gly Ala
                20                  25                  30

Met Ile Lys Ser Gln Arg Gln Gln Pro Arg Gly Gly Gln Ala Lys Lys
                35                  40                  45

Lys Lys Pro Glu Lys Pro His Phe Pro Leu Ala Ala Glu Asp Asp Ile
    50                  55                  60

Arg His His Leu Thr Gln Thr Glu Arg Ser Leu Cys Leu Gln Ser Ile
65                  70                  75                  80

Gln Thr Ala Phe Asn Gln Gly Ala Gly Thr Ala Ser Leu Ser Ser Ser
                85                  90                  95

Gly Lys Val Ser Phe Gln Val Glu Phe Met Leu Pro Val Ala His Thr
                100                 105                 110

Val Arg Leu Ile Arg Val Thr Ser Thr Ser Ala Ser Gln Gly Ala Ser
        115                 120                 125

(2) INFORMATION FOR SEQ ID NO:27:

(i) SEQUENCE CHARACTERISTICS:
        (A) LENGTH: 50 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:27:

GAGAGAGAGA GAGAGAGAGA ACTAGTCTCG AGTTTTTTTT TTTTTTTTTT            50

(2) INFORMATION FOR SEQ ID NO:28:

(i) SEQUENCE CHARACTERISTICS:
        (A) LENGTH: 13 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:28:

AATTCGGCAC GAG                                                   13

(2) INFORMATION FOR SEQ ID NO:29:

(i) SEQUENCE CHARACTERISTICS:
        (A) LENGTH: 9 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:29:

CTCGTGCCG                                                                                              9

(2) INFORMATION FOR SEQ ID NO:30:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:30:

GTAAAACGAC GGCCAGT                                                                                    17

(2) INFORMATION FOR SEQ ID NO:31:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:31:

GCTGTTAAAC AGGGAGTGG                                                                                  19

(2) INFORMATION FOR SEQ ID NO:32:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:32:

GTCACCTATT CAATTAGGG                                                                                  19

(2) INFORMATION FOR SEQ ID NO:33:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:33:

CCCTAATTGA ATAGGTGAC                                                                                  19

(2) INFORMATION FOR SEQ ID NO:34:

(i) SEQUENCE CHARACTERISTICS:
        (A) LENGTH: 171 bases
        (B) TYPE: nucleic acid
        (C) STRANDEDNESS: single
        (D) TOPOLOGY: linear -continued (ii) MOLECULE TYPE: DNA (iii) HYPOTHETICAL: NO (xi) SEQUENCE DESCRIPTION: SEQ ID NO:34:

TGGGCTGGCA TTCTTGAGGC ATCTCAGTGT TTGAATTGGA AGAATGTGTG GTGAATGGCA      60

CTGATTGACA TTGTGCCTCT AAGTCACCTA TTCAATTAGG GCGACCGTGT GGGGGTGAGA     120

TTTAATTGGC GAGAACCATG CGGCCGAAAT TAAAAAAAAA AAAAAAAAA A              171

(2) INFORMATION FOR SEQ ID NO:35:

(i) SEQUENCE CHARACTERISTICS:
        (A) LENGTH: 135 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:35:

ATTTGACAGT CAGGTGAATG GCCGCGATTG GCGTGTGGCC TCTGAGTCAC CTATTCAATT      60

AGGGCGATCA CATGGGGGTC ATACTTAATC AGGCAGGAAC CATGTGACCG AAATTAAAAA     120

AAAAAAAAAA AAAAA                                                     135

What is claimed is:

1. An isolated DNA sequence encoding a protein, wherein the protein comprises an amino acid sequence selected from the group consisting of Sequence ID Nos. 3, 5, 7, 9, and 13.

2. An isolated DNA sequence comprising the full-length PRRSV- cDNA insert of a clone selected from the group consisting of clones 431, ATCC Accession Number 203083 and 712, ATCC Accession Number 203084.

3. A isolated clone selected from the group consisting of clones 431, ATCC Accession Number 203063 and 712, ATCC Accession Number 203084.

* * * * *